(12) United States Patent
Avery et al.

(10) Patent No.: US 7,468,445 B2
(45) Date of Patent: Dec. 23, 2008

(54) ANTIGIARDIAL AGENTS AND USE THEREOF

(75) Inventors: Mitchell Avery, Oxford, MS (US); Larry A. Walker, Oxford, MS (US); Nakul Telang, University, MS (US)

(73) Assignee: University of Mississippi, University, MS (US)

( * ) Notice: Subject to any disclaimer, the term of this patent is extended or adjusted under 35 U.S.C. 154(b) by 435 days.

(21) Appl. No.: 10/523,964

(22) PCT Filed: Aug. 7, 2003

(86) PCT No.: PCT/US03/24938

§ 371 (c)(1), (2), (4) Date: Feb. 7, 2005

(87) PCT Pub. No.: WO2004/014886

PCT Pub. Date: Feb. 19, 2004

(65) Prior Publication Data

US 2006/0106091 A1     May 18, 2006

Related U.S. Application Data

(60) Provisional application No. 60/401,664, filed on Aug. 7, 2002.

(51) Int. Cl.
    C07D 311/00    (2006.01)
    A01N 43/16     (2006.01)
(52) U.S. Cl. ................................ 549/399; 514/456
(58) Field of Classification Search ............. 549/399; 514/456
    See application file for complete search history.

(56) References Cited

U.S. PATENT DOCUMENTS

| | | | |
|---|---|---|---|
| 6,326,366 B1 | 12/2001 | Potter et al. | |
| 6,391,309 B1 | 5/2002 | Empie et al. | |
| 6,541,613 B2 | 4/2003 | Hendler et al. | |
| 6,592,910 B1 | 7/2003 | Banz et al. | |
| 6,593,310 B1 | 7/2003 | Cullis-Hill | |
| 6,599,536 B1 | 7/2003 | Kelly et al. | |

FOREIGN PATENT DOCUMENTS

| | | |
|---|---|---|
| EP | 0031885 | 11/1980 |
| EP | 0267155 | 10/1987 |
| EP | 0267155 A2 * | 10/1987 |
| WO | WO91/15483 | 10/1991 |
| WO | WO93/23069 | 11/1993 |
| WO | WO94/23716 | 10/1994 |
| WO | WO95/03293 | 2/1995 |
| WO | WO96/39832 | 12/1996 |
| WO | WO99/48496 | 9/1999 |
| WO | WO99/49862 | 10/1999 |
| WO | WO00/49009 | 8/2000 |
| WO | WO00/62765 | 10/2000 |
| WO | WO00/62774 | 10/2000 |
| WO | WO01/17986 | 3/2001 |
| WO | WO03/055860 | 7/2003 |

OTHER PUBLICATIONS

Shao et al. STN Accession No. 1981:174809; Document No. 94:174809; Yaoxue Xuebao (1980), 15(9), 538-47.*
Abdullaev; Antitrichomonas activity of different groups of substances isolated from the flora of Central Asia; Farmakol. Prir. Veschestv; 1978; pp. 103-107.
Adam, R. D. Biology of Giardia lamblia. Clinical Microbiology Reviews 2001, 14, 447-475.
Aghoramurthy, et al.; Chemical Abstract; Columbus, OH, US; J. Indian Chem. Soc; vol. 38; 1961; pp. 914-918.
Anand, et al.; Chemical Abstract; Columbus, OH, US; J. Sci. Ind. Research; vol. 15B, 1956; p. 263.
Angarano, et. al.; Giardiasis in HIV: a possible role in patients with severe immune deficiency. European Journal of Epidemiology 1997, 13, 485-487.
Arjmandi, B. H. The role of phytoestrogens in the prevention and treatment of osteoporosis in ovarian hormone deficiency. Journal of the American College of Nutrition 2001, 20, 398S-402S.
Barat, L. M.; Bloland, P. B. Drug resistance among malaria and other parasites. Infectious Disease Clinics of North America 1997, 11, 969-987.
Belmar, et al.; Synthesis of new mesogenic compounds having the isoflavone core group; Liquid Crystals; 1999; vol. 26(1); pp. 75-81.
Brandi, M. L. Phytoestrogens and menopause. Environmental Toxicology and Pharmacology 1999, 7, 213-216.
Brandi, M. L. Natural and synthetic isoflavones in the prevention and treatment of chronic diseases. Calcified Tissue International 1997, 61, S5-S8.
Calzada, F.; Meckes, M.; Cedillo-Rivera, R. Antiamoebic and antigiardial activity of plant flavonoids. Planta Medica 1999, 65, 78-80.
Calzada, et al; Geranins A and B, New Antiprotozoal A-Type Proanthocyanidins from *Geranium niveum*. Journal of Natural Products 1999, 62, 705-709.
Chakravarti, et al.; Chemical Abstracts; Columbus, OH, US; Sci. Cult; vol. 28; 1962; pp. 242-243.

(Continued)

*Primary Examiner*—D. Margaret Seaman
*Assistant Examiner*—Nizal S Chandrakumar
(74) *Attorney, Agent, or Firm*—Stites & Harbison PLLC; Richard S. Myers, Jr.

(57) ABSTRACT

The present invention provides a method of preventing or treating one or more of the following medical conditions, or treating symptoms of one or more of the following medical conditions: amebic infections, giardiasis, estrogen deficient states, osteoporosis, cardiovascular heart disease, high cholesterol levels, hyperlipidemia, cancer by administering to a subject having, or predisposed to, one or more of the conditions, a therapeutically effective amount of a compound of the present invention and a pharmaceutically acceptable carrier.

6 Claims, No Drawings

OTHER PUBLICATIONS

Chang, et al.; Excretion of radioactive daidzein and dquol as monosulfates and disulfates in the urine of the laying hen; CA J. Biochem; 1975; vol. 53(2); pp. 2230-230.

Chudgar, et al.; Studies in isoflavones. I. Bromination, iodination, and nitration of 7-hydroxyisoflavone. J. Inst. Chem. (India) 1967, 39, 203-208.

Della Valle, F.; Romeo, A. 2-Haloresorcinols. Eur. Pat. Appl.; (Fidia S.p.A., Italy). Ep, 1985, 31 pp.

ElSohly, et al.; Antigiardial isoflavones from *Machaerium aristulatum*. Planta Medica (1999), 65(5), 490.

Farkas, et al.; Chemical Abstract; Columbus, OH; Chem. Ber; vol. 91; 1958; pp. 2858-2861.

Gennari, C. Calcitonin, bone-active isoflavones and vitamin D metabolites. Osteoporosis International 1999, 9, 81-90.

Gillin, et al.; Cell biology of the primitive eukaryote *Giardia lamblia*. Annual Review of Microbiology 1996, 50, 679-705.

Goldwyn, et al.; Promotion of health by soy isoflavones: efficacy, benefit and safety concerns. Drug Metabolism and Drug Interactions 2000, 17, 261-289.

Harborne, et al.; Chemical Abstracts, Columbus, OH; J. Org. Chem; vol. 28; 1963; pp. 881-882.

Jain, et al.; Flavonoids from *Eschscholzia californica*; Phytochemistry; 1996; vol. 41(2); pp. 661-662.

Joshi, et al.; Studies in the synthesis of furochromones. Part VIII Synthesis of furoisoflavones; IN J. Chem. Sec B: Org Chem Incl Med Chem.; 1988; vol. 27B(9); pp. 806-810.

Kalra, et al; Synthesis of 2-hydroxyisoflavones; Indian J. Chem; vol. 5(7); 1967; pp. 287-290.

Keister, D. B. Axenic culture of *Giardia lamblia* in TYI-S-33 medium supplemented with bile. Transactions of the Royal Society of Tropical Medicine and Hygiene 1983, 77, 487-488.

Khan, et al.; Antigiardial Activity of Isoflavones from *Dalbergia frutescens* Bark. Journal of Natural Products 2000, 63, 1414-1416.

Khan, et al.; Antigiardial Activity of Isoflavones from *Dalbergia frutescens* Bark. Journal of Natural Products (2000), 63(10), 1414-1416.

Khilya, et al.; Reaction of isoflavones and their 4-thioxo analogs with hydroxylamine; Ukrainskii Khimicheskii Zhurnal (Russian Edition); 1990; vol. 56(3); pp. 280-286.

Khilya, et al.; Synthetic analogs of natural isoflavones; Ukrainskii Khimicheskii Zhurnal (Russian Edition); 1984; vol. 50(12); pp. 1301-1306.

Kiehlmann, E.; Lauener, R. W. Bromophloroglucinols and their methyl ethers. Can. J. Chem. 1989, 67, 335-344.

Kitagawa, et al.; Aryloxyacetic acid diuretics with uricosuric activity. II. Substituted "(4-oxo-4H-1-benzopyran-7-yl)oxylacetic acids and the related compounds; Chem & Pharm Bulletin; 1991; vol. 39(10); pp. 2681-2690.

Lal, G. S.; Pez, G. P.; Syvret, R. G. Electrophilic NF Fluorinating Agents. Chemical Reviews (Washington, D. C.) 1996, 96, 1737-1755.

Lehmann, et al; Studies on biological activity of isoflavones in cultivated V79 cells; Lebensmittelchemie; 1999; vol. 53(5); p. 124.

Lei, et al.; Synthesis and preliminary studies on bioactivities of 7-hydroxy-4'-methylisoflavone; Zhongguo Yaowu Huaxue Zazhi; 2001; vol. 11(5); pp. 270-273.

Levy, et al.; Surveillance for waterborne-disease outbreaks—United States, 1995-1996. Morbidity and Mortality Weekly Report. CDC Surveillance Summaries 1998, 47, 1-34.

Liao, et al.; Theoretical study of nuclear magnetic resonance spectra of isoflavone derivatives with m-substituents on B ring; Sichuan Shifan Daxue Xuebao, Ziran Kexueban; 2002; vol. 25(6); pp. 632-636.

Liu, et al.; 1H NMR studies on synthetic isoflavones with p-substituents on B ring; Gaodeng Xuexiao Huaxue Xuebao; 2000; vol. 21(1); pp. 1671-1674.

Liu, et al.; Studies on synthesis and antitumor activities of soybean isoflavones and their derivatives; Yaoxue Xuebao; 2000; vol. 35(8); pp. 583-586.

Luk 'Yanchikov, et al.; Synthesis of analogs of natural isoflavones via 2, 4-dihydroxydeoxybenzoins; Khimiya Prirodnykh Soedinenii; 1985; vol. 6; pp. 781-784.

Marshall, et al.; Waterborne protozoan pathogens. Clinical Microbiology Reviews 1997, 10, 67-85.

Meckes, M.; Calzada, F.; Tapia-Contreras, A.; Cedillo-Rivera, R. Antiprotozoal properties of *Helianthemum glomeratum*. Phytotherapy Research 1999, 13, 102-105.

Mineno, et al.; Solution-phase parallel synthesis of an isoflavone library for the discovery of novel antigiardial agents; Combinatorial Chemistry and High Throughput Screening; vol. 5(6); 2002; pp. 481-487.

Messina, M. Soyfoods and soybean phyto-estrogens (isoflavones) as possible alternatives to hormone replacement therapy (HRT). European Journal of Cancer 2000, 36, S71-S72.

Moolasart, P. *Giardia lamblia* in AIDS patients with diarrhea. Journal of the Medical Association of Thailand 1999, 82, 654-659.

Polkowski, K.; Mazurek, A. P. Biological properties of genistein a review of in vitro and in vivo data. Acta Poloniae Pharmaceutica 2000, 57, 135-155.

Ruenitz, P. C. Drugs of osteoporosis prevention: mechanisms of bone maintenance. Curr. Med. Chem. 1995, 2, 791-802.

Sepulveda-Boza, et al.; The preparation of new isoflavones; Synthetic Comm; 2001; vol. 32(12); pp. 1933-1940.

Shao, et al.; Studies on the synthesis and structure-antihypoxia activity relations of daidezein, an active principle of *Pueraria pseudohiruta*, and its derivatives; Yaoxue Xuebao; 1989; vol. 15(9); pp. 538-547.

Shirataki, et al.; Relationship between cytotoxic activity and radical intensity of isoflavones from Sphora species; Anticancer Research; 2001; vol. 21(4A); pp. 2643-2648.

Sun, W.-C.; Gee, K. R.; Klaubert, D. H.; Haugland, R. P. Synthesis of fluorinated fluoresceins. Journal of Organic Chemistry 1997, 62, 6469-6475.

Suthar, A. C.; Banavalikar, M. M.; Biyani, M. K. Pharmacological activities of genistein, an isoflavone from soy (Glycine max): Part II-Anti-cholesterol activity, effects on osteoporosis & menopausal symptoms. Indian Journal of Experimental Biology 2001, 39, 520-525.

Traxler, et al.; Use of a Pharmacophore Model for the Design of EGFR Tyrosine Kinase Inhibitors: Isoflavones and 3-Phenyl-4(1H)-quinolones; J. Medicinal Chem; 1999; vol. 42(6); pp. 1018-1026.

Upcroft, P.; Upcroft, J. A. Drug targets and mechanisms of resistance in the anaerobic protozoa. Clinical Microbiology Reviews 2001, 14, 150-164.

Varga, et al.; Stability and chemical reactivity of 7-isopropoxyisoflavone (ipriflavone); European J. of Organic Chem; 2001; vol. 20; pp. 3911-3920.

Vasil'Ev, et al.; Synthesis and anabolic action of modified isoflavones; Khimiko-Farmatsevticheskii Zhurnal; 1990; vol. 24(9); pp. 38-41.

Vesy, C. J.; Peterson, W. L. Review article: the management of Giardiasis. Alimentary Pharmacology and Therapeutics 1999, 13, 843-850.

Waehaelae, et al; Synthesis and labeling of isoflavone phytoestrogens, including daidzein and genistein; Proceedings of the Society for Experimental Bio and Med; 1995; vol. 208(1); pp. 27-32.

Wahala, K.; Hase, T. A. Expedient synthesis of polyhydroxyisoflavones. J. Chem. Soc., Perkin Trans. I 1991, 3005-3008.

Wilson, M. E. Public Health & Preventive Medicine; 14th ed.; Appleton & Lange: Stamford, CT, 1998; pp pp. 252-254.

Wright, C. W.; Melwani, S. I.; Phillipson, J. D.; Warhurst, D. C. Determination of anti-giardial activity in vitro by means of soluble formazan production. Trans. R. Soc. Trop. Med. Hyg. 1992, 86, 517-519.

Yamaguchi, M. Isoflavone and bone metabolism: its cellular mechanism and preventive role in bone loss. Journal of Health Science 2002, 48, 209-222.

Yang, J.-J.; Su, D.; Vij, A.; Hubler, T. L.; Kirchmeier, R. L.; Shreeve, J. n. M. Synthesis of 4-fluororesorcinol and 4-trifluoromethylresorcinol. Heteroatom Chemistry 1998, 9, 229-239.

Yi, et al.; Studies on chemical constituents of Smilax glabra Robx. (IV); Yaoxue Xuebao; 1998; vol. 33(11); pp. 873-875.

Yue, et al.; Studies on flavonoids; VI. Synthesis of the 8-bromo-4',7-dihydroxyisoflavone; Gaodeng Xuexiao Huaxue Xuebao; 1988; vol. 9(3); pp. 292-294.

Yue, et al.; Studies on flavonoids; XIV. Debromination reaction in the synthesis of bromoisoflavones; Gaodeng Xuexiao Huaxue Xuebao; 1990; vol. 11(1); pp. 99-101.

* cited by examiner

ANTIGIARDIAL AGENTS AND USE THEREOF

PRIORITY CLAIM

This Application claims priority to U.S. Application No. 60/401,664, filed Aug. 7, 2002, the contents of which are incorporated herein by reference.

UNITED STATES GOVERNMENT SUPPORT

This work is a result of research sponsored in part by the Center for Disease Control Grant # U50/CCU41839. The United States Government has certain rights in this invention.

TECHNICAL FIELD OF THE INVENTION

The present invention relates to novel compounds and a method of treating or preventing certain medical clinical conditions with the compounds of the present invention. In particular, the method of the present invention includes preventing or treating giardiasis and giardiasis-related infections, including amebic (protozoal) infections, as well as osteoporosis, cardiovascular disease, high cholesterol, hyperlipidemia.

BACKGROUND OF THE INVENTION

*Giardia lamblia* (also known as *Giardia intestinalis*) is a flagellated unicellular protozoan that causes acute or chronic gastrointestinal disease, giardiasis, in humans and mammals. The parasite is protected by an outer shell that allows it to survive outside the body and in the environment for long periods of time. The parasite is found in every region of the United States and throughout the world, infecting over 200 million people are infected with *Giardia* throughout the world. Although becoming one of the most commonly recognized causes of waterborne disease (drinking and recreational) in humans in the United States, Giardiasis is more widespread in the developing countries where infection is correlated with poor hygienic conditions, poor water quality control, and overcrowding. Also, the prevalence of diarrhea caused by *G. lamblia* in AIDS patients is higher than those without AIDS due to suppressed immunity in AIDS patients.

The treatment of giardiasis has changed over the past 5 years. Quinacrine (1, below) was previously used until 1998 when its manufacture was halted in the United States. The current mainstay of treatment for giardiasis is metronidazole (2, below) with reported cure rates of 80 to 95%. However, due to general toxicity and occasional drug resistance to metronidazole, an ongoing search for novel, safe, and efficacious antigiardial agents is required.

Biological evaluation of various natural products has indicated that molecules possessing a flavonoid skeleton such as geranins A (3, below) and B (4, below), kaempferol (5, below), and quercetin (6, below) exhibit antigiardial activity. Also, formononetin (7, below) and pseudobaptigenin (8, below) have been shown to possess potent antigiardial activity in vitro.

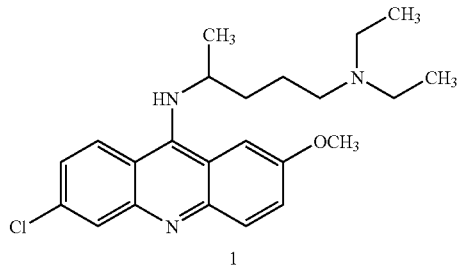

1

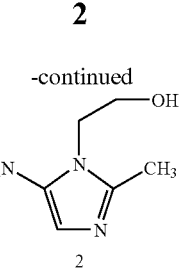

2

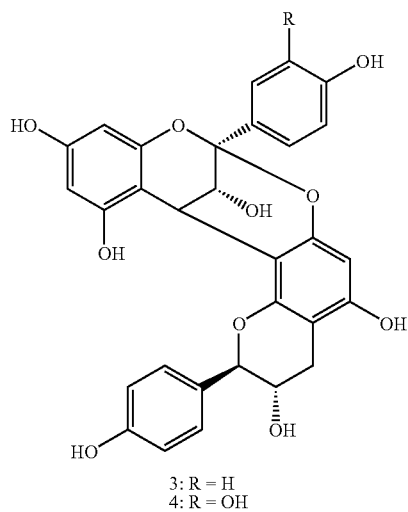

3: R = H
4: R = OH

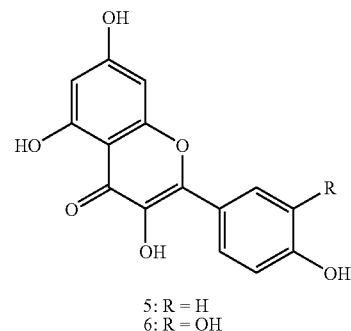

5: R = H
6: R = OH

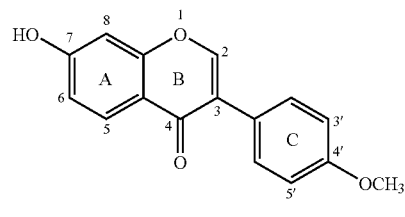

7

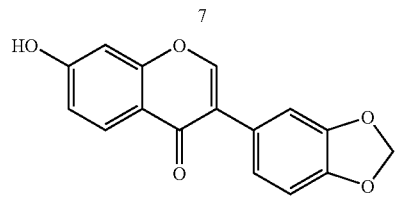

8

In view of these results, the present inventor developed the isoflavone derivatives of the present invention as an approach to discover a potent lead while simultaneously developing structure-activity relationships (SAR).

The isoflavones are a group of naturally occurring plant compounds having the aromatic heterocyclic skeleton of isoflavone itself (2-phenyl-4H-benzopyran-4-one). Soybeans are the most common and well known source of isoflavones, reported to contain the isoflavones, daidzin, genistin, glycitin, 6"-dadidzin-O-acetyl, 6"-O-acetyl genistin, 6"-O-malonyl daidzin, and 6"-O-malonyl genistin. Isoflavones are present in processed soy foods as well, including miso and soy sauce. Legumes, lupine, fava bean, kudzu and psoralea may also be important sources. The existence of isoflavones in Pueraria has long been known, with the roots of Pueraria containing several isoflavone compounds, such as daidzin, and puerarin. Even isoflavone itself has been isolated from *Primula malacoides*.

Isoflavones are known in aglucone forms, as well as 7-acetylated and 7-substituted glycosides. Especially important isoflavones in aglucone form include daidzein, genistein, and glycitein. Especially important isoflavones in 7-glycoside form include daidzin, genistin, and glycitin. Genistein is also known to occur naturally as a 4'-glucoside (sophoricoside), and a 4'-methyl ether (biochanin A).

Isoflavones in general, and genistein in particular, have structural similarities to that of certain human estrogens, and such compounds are said to have estrogenic activity. Isoflavones are also said to have other useful biological and pharmacological activities, including antiangiogenic, antihemolytic, antiischemic, antileukemic, antimitogenic, antimutagenic, antioxidant, fungicidal, pesticidal, MAO-inhibition, phytoalexin, and tyrosine kinase inhibition activities.

The anticancer effects of genistein are of particular interest. Genistein may exert antitumor effects in part by inhibiting angiogenesis, i.e., reducing formation of vasulature and blood flow to the tumor. Its affinity to estrogenic sites in the vicinity of cancer cells may also inhibit tumor growth. As a well-known inhibitor of the enzyme tyrosine kinase, genistein may also inhibit energy and signaling pathways in tumors.

Genistein and other isoflavones are also said to be important contributors to bone health, resulting at least in part from the ability of these compounds to inhibit protein kinase activity, and thereby inhibit osteoclast cell activity. The isoflavones are especially attractive in this regard because they generally have a low toxicity relative to many other known protein kinase inhibitors.

Because of its many beneficial effects, enriched sources of genistein are marketed to consumers around the world in a wide variety of nutritional supplements. Many of the health benefits of soy products are ascribed to the presence of genistein.

More specifically, isoflavones have been linked to the following conditions and/or treatments:

Osteoporosis: Osteoporosis is a systemic skeletal disease, characterized by low bone mass and deterioration of bone tissue, with a consequent increase on bone fragility and susceptibility to fracture. See U.S. Pat. No. 6,593,310. Isoflavones have been shown to prevent postmenopausal bone loss and osteoporosis. In fact, genistein has been reported to be as active as estrogens in maintaining bone mass in ovariectomized rats. Moreover, the synthetic isoflavone derivative ipriflavone is able to reduce bone loss in various types of animal models, providing a rationale on its use in the prevention and treatment of post-menopausal and senile osteoporosis in humans. The mechanism through which isoflavones may exert the above-mentioned effects seems to depend, at least in part, on their mixed estrogen agonist-antagonist properties. An alternative hypothetical mechanism could derive from other biochem actions of isoflavones such as inhibition of enzymic activity, in particular protein kinases, or activation of an "orphan" receptor distinct from the estrogen type I receptor.

Hormone Replacement: Ovarian hormone deficiency is a major risk factor for osteoporosis in postmenopausal women. Hormone replacement therapy (HRT) is perhaps the most effective treatment, as it has been demonstrated to both reduce the rate of bone loss and risk of fracture, including hip fracture.

As used herein, the term "hormone replacement therapy" means a treatment of a human female having reduced levels of endogenous estrogen in which a mammalian estrogen is administered to the female in combination with at least one other compound, where the other compound is administered to inhibit the estrogen's tissue proliferative effects in the breast or uterus. See U.S. Pat. No. 6,326,366.

However, not all women who may benefit from HRT are willing to initiate this treatment due to fear of cancer and contraindications. Other therapeutic agents currently available are also associated with certain adverse effects. As a result, postmenopausal women are more inclined to use natural remedies such as isoflavones to alleviate postmenopausal symptoms and help reduce their risk for chronic diseases such as osteoporosis. Recent reports support the notion that certain bioactive constituents, e.g., phytoestrogens, in plants play a role in maintaining or improving skeletal health.

Cardiovascular Disease: Isoflavones, including genistein in various types of diseases such as osteoporosis, cardiovascular diseases, menopausal symptoms by accumulating evidence from mol. and cellular biol. expts., animal studies, and, to a limited extent, human clin. trials. This review suggests that phytoestrogens may potentially confer health benefits related to various diseases such as cardiovascular disorder, menopausal symptoms, and osteoporosis.

Antiproliferative Effects: Isoflavones, such as genistein, have been found to be a potent agent in both prophylaxis and treatment of cancer as well as other chronic diseases. The great interest that has focused on genistein led to the identification of numerous intracellular targets of its action in the live cell. At the molecular level, genistein inhibits the activity of ATP utilizing enzymes such as: Tyr-specific protein kinases, topoisomerase II, and enzymes involved in phosphatidylinositol turnover. Moreover, genistein can act via an estrogen receptor-mediated mechanism. At the level 1 step higher, i.e., at the cellular level, genistein induces apoptosis and differentiation in cancer cells, inhibits cell proliferation, modulates cell cycling, exerts antioxidant effects, inhibits angiogenesis, and suppresses osteoclast and lymphocyte functions. These activities make genistein a promising innovative agent in the treatment of cancer. Additionally, genistein health beneficial effects were shown in osteoporosis, cardiovascular diseases, and menopause. Genistein was also successfully used as an immunosuppressive agent both in vitro and in vivo. All these effects at the 3 biol. levels of action need varied genistein concns. and only some of them are relevant in people consuming soy-rich diet. The others would occur after purified genistein administration at higher doses. The main genistein advantage as a potential drug is its multidirectional action in the live cell and its very low toxicity.

The present inventor has discovered that the compounds of the present invention possess the benefits and usefulness of isoflavone, but are advantageous in that, among other things, have increased bioavailability and are more easily synthesized.

To more fully describe the state of the art to which this invention pertains, the following references are provided:

Adam, R. D. Biology of *Giardia lamblia*. Clinical Microbiology Reviews 2001, 14, 447-475.

Gillin, F. D.; Reiner, D. S.; McCaffery, J. M. Cell biology of the primitive eukaryote *Giardia*

Barat, L. M.; Bloland, P. B. Drug resistance among malaria and other parasites. INFECTIOUS DISEASE CLINICS OF NORTH AMERICA 1997, 11, 969-987.

Wilson, M. E. Public Health & Preventive Medicine; 14th ed.; Appleton & Lange: Stamford, Conn., 1998; pp pp. 252-254.

Vesy, C. J.; Peterson, W. L. Review article: the management of Giardiasis. ALIMENTARY PHARMACOLOGY AND THERAPEUTICS 1999, 13, 843-850.

Marshall, M. M.; Naumovitz, D.; Ortega, Y.; Sterling, C. R. Waterborne protozoan pathogens. Clinical Microbiology Reviews 1997, 10, 67-85.

Levy, D. A.; Bens, M. S.; Craun, G. F.; Calderon, R. L.; Herwaldt, B. L. Surveillance for waterborne-disease outbreaks—United States, 1995-1996. MORBDITY AND MORTALITY WEEKLY REPORT. CDC SURVEILLANCE SUMMARIES 1998, 47, 1-34.

Moolasart, P. *Giardia lamblia* in AIDS patients with diarrhea. JOURNAL OF THE MEDICAL ASSOCIATION OF THAILAND 1999, 82, 654-659.

Angarano, G.; Maggi, P.; Di Bari, M. A.; Larocca, A. M.; Congedo, P.; Di Bari, C.; Brandonisio, O.; Chiodo, F. Giardiasis in HIV: a possible role in patients with severe immune deficiency. EUROPEAN JOURNAL OF EPIDEMIOLOGY 1997, 13, 485-487.

Upcroft, P.; Upcroft, J. A. Drug targets and mechanisms of resistance in the anaerobic protozoa. Clinical Microbiology Reviews 2001, 14, 150-164.

Calzada, F.; Cerda-Garcia-Rojas, C. M.; Meckes, M.; Cedillo-Rivera, R.; Bye, R.; Mata, R. Geranins A and B, New Antiprotozoal A-Type Proanthocyanidins from *Geranium niveum*. Journal of Natural Products 1999, 62, 705-709.

Meckes, M.; Calzada, F.; Tapia-Contreras, A.; Cedillo-Rivera, R. Antiprotozoal properties of *Helianthemum glomeratum*. Phytotherapy Research 1999, 13, 102-105.

Calzada, F.; Meckes, M.; Cedillo-Rivera, R. Antiamoebic and antigiardial activity of plant flavonoids. PLANTA MEDICA 1999, 65, 78-80.

Khan, I. A.; Avery, M. A.; Burandt, C. L.; Goins, D. K.; Mikell, J. R.; Nash, T. E.; Azadegan, A.; Walker, L. A. Antigiardial Activity of Isoflavones from *Dalbergia frutescens* Bark. Journal of Natural Products 2000, 63, 1414-1416.

Brandi, M. L. Natural and synthetic isoflavones in the prevention and treatment of chronic diseases. Calcified Tissue International 1997, 61, S5-S8.

Ruenitz, P. C. Drugs for osteoporosis prevention: mechanisms of bone maintenance. Curr. Med. Chem. 1995, 2, 791-802.

Gennari, C. Calcitonin, bone-active isoflavones and vitamin D metabolites. Osteoporosis International 1999, 9, 81-90.

Yamaguchi, M. Isoflavone and bone metabolism: its cellular mechanism and preventive role in bone loss. Journal of Health Science 2002, 48, 209-222.

Arjmandi, B. H. The role of phytoestrogens in the prevention and treatment of osteoporosis in ovarian hormone deficiency. Journal of the American College of Nutrition 2001, 20, 398S-402S.

Messina, M. Soyfoods and soybean phyto-estrogens (isoflavones) as possible alternatives to hormone replacement therapy (HRT). European Journal of Cancer 2000, 36, S71-S72.

Brandi, M. L. Phytoestrogens and menopause. Environmental Toxicology and Pharmacology 1999, 7, 213-216.

Suthar, A. C.; Banavalikar, M. M.; Biyani, M. K. Pharmacological activities of genistein, an isoflavone from soy (*Glycine max*): Part II-Anti-cholesterol activity, effects on osteoporosis & menopausal symptoms. Indian Journal of Experimental Biology 2001, 39, 520-525.

Polkowski, K.; Mazurek, A. P. Biological properties of genistein a review of in vitro and in vivo data. Acta Poloniae Pharmaceutica 2000, 57, 135-155.

Goldwyn, S.; Lazinsky, A.; Wei, H. Promotion of health by soy isoflavones: efficacy, benefit and safety concerns. Drug Metabolism and Drug Interactions 2000, 17, 261-289.

Sun, W.-C.; Gee, K. R.; Klaubert, D. H.; Haugland, R. P. Synthesis of fluorinated fluoresceins. Journal of Organic Chemistry 1997, 62, 6469-6475.

Della Valle, F.; Romeo, A. 2-Haloresorcinols. Eur. Pat. Appl.; (Fidia S.p.A., Italy). Ep, 1985, 31 pp.

Kiehlmann, E.; Lauener, R. W. Bromophloroglucinols and their methyl ethers. Can. J. Chem. 1989, 67, 335-344.

Yang, J.-J.; Su, D.; Vij, A.; Hubler, T. L.; Kirchmeier, R. L.; Shreeve, J. n. M. Synthesis of 4-fluororesorcinol and 4-trifluoromethylresorcinol. Heteroatom Chemistry 1998, 9, 229-239.

Lal, G. S.; Pez, G. P.; Syvret, R. G. Electrophilic NF Fluorinating Agents. Chemical Reviews (Washington, D.C.) 1996, 96, 1737-1755.

Wahala, K.; Hase, T. A. Expedient synthesis of polyhydroxyisoflavones. J. Chem. Soc., Perkin Trans. 1 1991, 3005-3008.

Keister, D. B. Axenic culture of *Giardia lamblia* in TYI-S-33 medium supplemented with bile. TRANSACTIONS OF THE ROYAL SOCIETY OF TROPICAL MEDICINE AND HYGIENE 1983, 77, 487-488.

Wright, C. W.; Melwani, S. I.; Phillipson, J. D.; Warhurst, D. C. Determination of anti-giardial activity in vitro by means of soluble formazan production. Trans. R. Soc. Trop. Med. Hyg. 1992, 86, 517-519.

Chudgar, N. K.; Mani, N. V.; Sethna, S. Studies in isoflavones. I. Bromination, iodination, and nitration of 7-hydroxyisoflavone. J. Inst. Chem. (India) 1967, 39, 203-208.

Khan, Ikhlas A.; Avery, Mitchell A.; Goins, D. Keith; Walker, Larry A.; Burandt, Charles L. Isoflavones for treating giardiasis and malaria PCT Int. Appl. (1999), 16 pp. WO 9949862 A1 19991007

ElSohly, Hala N.; Joshi, A. S.; Nimrod, A. C. Antigiardial isoflavones from *Machaerium aristulatum*. Planta Medica (1999), 65(5), 490.

Khan, I. A.; Avery, M. A.; Burandt, C. L.; Goins, D. K; Mikell, J. R; Nash, T. E.; Azadegan, A.; Walker, L. A. Antigiardial Activity of Isoflavones from *Dalbergia frutescens* Bark. Journal of Natural Products (2000), 63(10), 1414-1416.

U.S. Pat. Nos. 6,593,310; 6,326,366; 6,592,910; 6,599,536; 6,391,309; 6,541,613.

SUMMARY OF THE INVENTION

The present invention provides a method of preventing or treating one or more of the following medical conditions, or treating symptoms of one or more of the following medical conditions: amebic infections, giardiasis, estrogen deficient states, osteoporosis, cardiovascular heart disease, high cholesterol levels, hyperlipidemia, cancer.

The present invention further provides a method or preventing or treating the symptoms of one or more of the aforementioned medical conditions by administering to a subject having, or predisposed to, one or more of the conditions, a therapeutically effective amount of a compound of the present invention and a pharmaceutically acceptable carrier.

DESCRIPTION OF THE INVENTION

As stated above, the compounds of the present invention are useful for treating and/or preventing various medical conditions. In particular, the compounds of the present invention are useful in the treatment and prevention of giardial (giardiasis) or other amebic (protozoal) infections. Compounds of the present invention are also useful in the treatment of estrogen deficient states such as the chronic treatment of osteoporosis, and for pre- and post-menopausal estrogen replacement therapy. They can be useful as cardioprotective agents in controlling the progression of cardiovascular heart disease, and for lowering cholesterol levels and treating hyperlipidemia. Further, compounds of the present invention have antiproliferative anticancer activity, and cancer preventative utility.

The compounds of the present invention may be readily synthesized and optimized for a particular property by parallel methods either on solid-phase or in solution-phase, or can be prepared as combinatorial libraries. Identified single compounds are easily synthesized by a variety of economically feasible methods well known in the art.

The compounds of the present invention are useful in the treatment of acute infections of giardiasis, tricomoniasis, shyphilitc disease, and other protozoan or amebic diseases; treatment of chronic osteoporosis due to low estrogen levels in pre and postmenopausal women; treatment of proliferative disorders such as cancer of the pro state, breast, ovary, uterus, testes and other tissues; for estrogen replacement therapy in low-hormone or postmenopausal women; as a cardioprotective agent in coronary artery disease; a mediator of cholesterol and lipid levels; and as a cancer preventative agent.

Compounds of the present invention include those listed below, as Formulae I-VI:

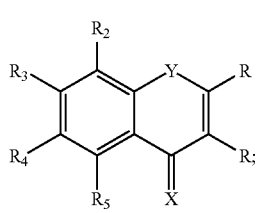

Formula I

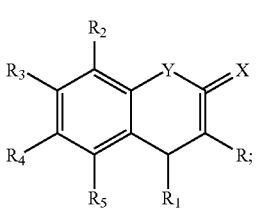

Formula II

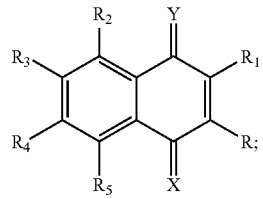

Formula III

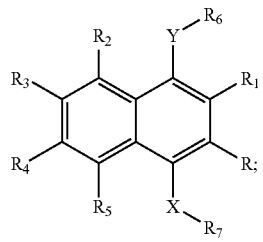

Formula IV

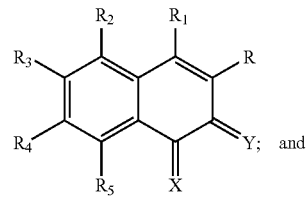

Formula V

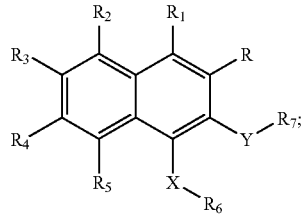

Formula VI wherein:
R, and $R_1$-$R_5$ are each independently be H, a lone pair of electrons, halogen, alkyl, aryl, amino, a Het group, N, O, S, SO, $SO_2$, $SO_2NH$, COO—, CONH—, COS—, CONR—, and C=O, each substituent being substituted or unsubstituted.

The substituents include alkyl, heterosubstituted alkyl, cycloalkyl, alkenyl, heterosubstituted alkenyl, cycloalkenyl, alkenyl, heterosubstituted alkynyl, heteroaryl, heterocyclic, arylalkyl, heterosubstitutedaryl, arylalkenyl, heterosubstituted alkenylaryl, arylalkynyl, heterosubstituted alkynylaryl, alkylheteroaryl, heterosubstituted alkylheteroaryl, alkenylheteroaryl, heterosubstituted alkenylheteroaryl, alkylheterocyclic, heterosubstitutedalkyl-heterocyclic, alkenylheterocyclic, and heterosubstitutedalkenyl-heterocyclic systems.

X is O, S, NR, NH, N-Aryl or N-Het.
Y is O, S, NR, NH, N-Aryl or N-Het, $NSO_2R$, $NSO_2Ar$.

With respect to Formulae IV and VI, $R_6$ and $R_7$ have the same definition as $R_{1-5}$, above, and X is O, S, SO, $SO_2$, $SONHR_8$, $SO_2NR_9R_{10}$, NR, NH, NAryl, N-Het, $NSO_2R$, $NSO_2Ar$, wherein $R_{8-10}$ have the same definition as $R_{1-5}$, above, in addition to $R_9$ and $R_{10}$ also being able to form an aryl or Het ring. Y is O, S, SO, SO$_2$, SONHR$_8$, SO$_2$NR$_9$R$_{10}$, NR, NH, NAryl, N-Het, NSO$_2$R, NSO$_2$Ar, wherein R$_{8-10}$ have the same definition as above.

Embodiments of the present invention including the following compounds of Formula VII:

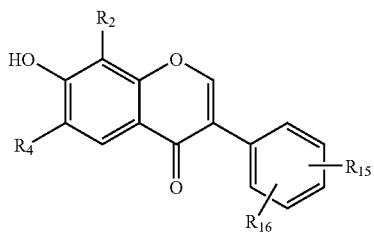

Formula VII wherein R$_2$ and R$_4$ are each independently H, allyl, halo.

R$_{15}$ and R$_{16}$ are each independently H, alkyl, acyl, alkoxy, aryl, amino, HET.

As discussed further below, the compounds of the present invention may be used in pharmaceutical compositions, comprising a compound of the present invention and a pharmaceutically acceptable carrier.

Additionally, the compounds of the present invention can be targeted for delivery to the intestine by prodrug formation such as to a polymeric material, or by incorporation into a hydrogel. The term "prodrug" used herein refers to a compound that can be metabolized to form a second compound of interest. Typical prodrugs include glucopyranosides of a functional group such as a phenolic group, esters, carbonates, and urethanes.

As used herein, the term alkyl or alkyl group is to be understood in the broadest sense to mean hydrocarbon residues which can be linear, i.e., straight-chain, or branched, and can be acyclic or cyclic residues or comprise any combination of acyclic and cyclic subunits. Further, the term alkyl as used herein expressly includes saturated groups as well as unsaturated groups which latter groups contain one or more, for example, one, two, or three, double bonds and/or triple bonds. The term alkyl includes substituted and unsubstituted alkyl groups.

All these statements also apply if an alkyl group carries substituents or occurs as a substituent on another residue, for example, in an alkyloxy residue, or an arylalkylamino residue. Examples of alkyl residues containing from 1 to 20 carbon atoms are methyl, ethyl, propyl, butyl, pentyl, hexyl, heptyl, octyl, nonyl, decyl, undecyl, dodecyl, tetradecyl, hexadecyl, octadecyl, and eicosyl, the n-isomers of all these residues, isopropyl, isobutyl, 1-methylbutyl, isopentyl, neopentyl, 2,2-dimethylbutyl, 2-methylpentyl, 3-methylpentyl, isohexyl, 2,3,4-trimethylhexyl, isodecyl, sec-butyl, tert-butyl, or tert-pentyl.

Unsaturated alkyl residues are, for example, alkenyl residues such as vinyl, 1-propenyl, 2-propenyl (=allyl), 2-butenyl, 3-butenyl, 2-methyl-2-butenyl, 3-methyl-2-butenyl, 5-hexenyl, or 1,3-pentadienyl, or alkynyl residues such as ethynyl, 1-propynyl, 2-propynyl (=propargyl), or 2-butynyl. Alkyl residues can also be unsaturated when they are substituted.

Examples of cyclic alkyl residues are cycloalkyl residues containing 3, 4, 5, 6, 7, or 8 ring carbon atoms like cyclopropyl, cyclobutyl, cyclopentyl, cyclohexyl, cycloheptyl, or cyclooctyl which can also be substituted and/or unsaturated. Unsaturated cyclic alkyl groups and unsaturated cycloalkyl groups like, for example, cyclopentenyl or cyclohexenyl can be bonded via any carbon atom. The term alkyl as used herein also comprises cycloalkyl-substituted alkyl groups like cyclopropylmethyl-, cyclobutylmethyl-, cyclopentylmethyl-, cyclohexylmethyl-, cycloheptylmethyl-, cyclooctylmethyl-, 1-cyclopropylethyl-, 1-cyclobutylethyl-, 1-cyclopentylethyl-, 1-cyclohexylethyl-, 1-cycloheptylethyl-, 1-cyclooctylethyl-, 2-cyclopropylethyl-, 2-cyclobutylethyl-, 2-cyclopentylethyl-, 2-cyclohexylethyl-, 2-cycloheptylethyl-, 2-cyclooctylethyl-, 3-cyclopropylpropyl-, 3-cyclobutylpropyl-, 3-cyclopentylpropyl-, 3-cyclohexylpropyl-, 3-cycloheptylpropyl-, or 3-cyclooctylpropyl- in which groups the cycloalkyl subgroup as well as acyclic subgroup also can be unsaturated and/or substituted.

Of course, a group like (C$_1$-C$_8$)-alkyl is to be understood as comprising, among others, saturated acyclic (C$_1$-C$_8$)-alkyl, (C$_3$-C$_8$)-cycloalkyl, cycloalkyl-alkyl groups like (C$_3$-C$_7$)-cycloalkyl-(C$_1$-C$_5$)-alkyl- wherein the total number of carbon atoms can range from 4 to 8, and unsaturated (C$_2$-C$_8$)-alkyl like (C$_2$-C$_8$)-alkenyl or (C$_2$-C$_8$)-alkynyl. Similarly, a group like (C$_1$-C$_4$)-alkyl is to be understood as comprising, among others, saturated acyclic (C$_1$-C$_4$)-alkyl, (C$_3$-C$_4$)-cycloalkyl, cyclopropyl-methyl-, and unsaturated (C$_2$-C$_4$)-alkyl like (C$_2$-C$_4$)-alkenyl or (C$_2$-C$_4$)-alkynyl.

Unless stated otherwise, the term alkyl preferably comprises acyclic saturated hydrocarbon residues containing from 1 to 6 carbon atoms which can be linear or branched, acyclic unsaturated hydrocarbon residues containing from 2 to 6 carbon atoms which can be linear or branched like (C$_2$-C$_6$)-alkenyl and (C$_2$-C$_6$)-alkynyl, and cyclic alkyl groups containing from 3 to 8 ring carbon atoms, in particular from 3 to 6 ring carbon atoms. A particular group of saturated acyclic alkyl residues is formed by (C$_1$-C$_4$)-alkyl residues like methyl, ethyl, n-propyl, isopropyl, n-butyl, isobutyl, sec-butyl, and tert-butyl.

The alkyl groups (and all other substitutent groups (aryl, amino, etc.)) of the present invention can in general be unsubstituted or substituted by one or more, for example, one, two, three, or four, identical or different substituents. Any kind of substituents present in substituted alkyl residues can be present in any desired position provided that the substitution does not lead to an unstable molecule. Examples of substituted alkyl residues are alkyl residues in which one or more, for example, 1, 2, 3, 4, or 5, hydrogen atoms are replaced with halogen atoms.

Examples of substituted cycloalkyl groups are cycloalkyl groups which carry as substituent one or more, for example, one, two, three, or four, identical or different acyclic alkyl groups, for example, acyclic (C$_1$-C$_4$)-alkyl groups like methyl groups. Examples of substituted cycloalkyl groups are 4-methylcyclohexyl, 4-tert-butylcyclohexyl, or 2,3-dimethylcyclopentyl.

The term aryl refers to a monocyclic or polycyclic hydrocarbon residue in which at least one carbocyclic ring is present. In a (C$_6$-C$_{14}$)-aryl residue from 6 to 14 ring carbon atoms are present. Examples of (C$_6$-C$_{14}$)-aryl residues are phenyl, naphthyl, biphenylyl, fluorenyl, or anthracenyl. Examples of (C$_6$-C$_{10}$)-aryl residues are phenyl or naphthyl. Unless stated otherwise, and irrespective of any specific substituents bonded to aryl groups, aryl residues including, for example, phenyl, naphthyl, and fluorenyl, can in general be unsubstituted or substituted by one or more, for example, one, two, three, or four, identical or different substituents. Aryl residues can be bonded via any desired position, and in substituted aryl residues the substituents can be located in any desired position.

In monosubstituted phenyl residues, the substituent can be located in the 2-position, the 3-position, or the 4-position, the 3-position and the 4-position being preferred. These positional nomenclatures (numbering schemes) refer to the residue itself, for the isoflavone ring system is itself numbered starting from O-1 to C-2, . . . C-4a, C-5, and so on up to C-8a. The C-2 phenyl ring of an isoflavone is numbered with prime numbers. Thus, formonnonetin 7 possess a 4'-methoxy group. If a phenyl group carries two substituents, they can be located in 2,3-position, 2,4-position, 2,5-position, 2,6-position, 3,4-position, or 3,5-position. In phenyl residues carrying three substituents, the substituents can be located in 2,3,4-position, 2,3,5-position, 2,3,6-position, 2,4,5-position, 2,4,6-position, or 3,4,5-position. Naphthyl residues can be 1-naphthyl and 2-naphthyl. In substituted naphthyl residues, the substituents can be located in any positions, for example, in monosubstituted 1-naphthyl residues in the 2-, 3-, 4-, 5-, 6-, 7-, or 8-position and in monosubstituted 2-naphthyl residues in the 1-, 3-, 4-, 5-, 6-, 7-, or 8-position. Biphenylyl residues can be 2-biphenylyl, 3-biphenylyl, or 4-biphenylyl. Fluorenyl residues can be 1-, 2-, 3-, 4, or 9-fluorenyl. In monosubstituted fluorenyl residues, bonded via the 9-position the substituent is preferably present in the 1-, 2-, 3-, or 4-position.

Unless stated otherwise, substituents that can be present in substituted aryl groups are, for example, $(C_1-C_8)$-alkyl, in particular $(C_1-C_4)$-alkyl, such as methyl, ethyl, or tert-butyl, hydroxy, $(C_1-C_8)$-alkyloxy, in particular $(C_1-C_4)$-alkyloxy, such as methoxy, ethoxy, or tert-butoxy, methylenedioxy, ethylenedioxy, F, Cl, Br, I, cyano, nitro, trifluoromethyl, trifluoromethoxy, hydroxymethyl, formyl, acetyl, amino, mono- or di-$(C_1-C_4)$-alkylamino, $((C_1-C_4)$-alkyl)carbonylamino like acetylamino, hydroxycarbonyl, $((C_1-C_4)$-alkyloxy) carbonyl, carbamoyl, optionally substituted phenyl, benzyl optionally substituted in the phenyl group, optionally substituted phenoxy, or benzyloxy optionally substituted in the phenyl group.

The above statements relating to aryl groups correspondingly apply to divalent residues derived from aryl groups, i.e., to arylene groups like phenylene which can be unsubstituted or substituted 1,2-phenylene, 1,3-phenylene, or 1,4-phenylene, or naphthalene which can be unsubstituted or substituted 1,2-naphthalenediyl, 1,3-naphthalenediyl, 1,4-naphthalenediyl, 1,5-naphthalenediyl, 1,6-naphthalenediyl, 1,7-naphthalenediyl, 1,8-naphthalenediyl, 2,3-naphthalenediyl, 2,6-naphthalenediyl, or 2,7-naphthalenediyl.

The above statements also correspondingly apply to the aryl subgroup in arylalkyl-groups. Examples of arylalkyl-groups which can also be unsubstituted or substituted in the aryl subgroup as well as in the alkyl subgroup, are benzyl, 1-phenylethyl, 2-phenylethyl, 3-phenylpropyl, 4-phenylbutyl, 1-methyl-3-phenyl-propyl, 1-naphthylmethyl, 2-naphthylmethyl, 1-(1-naphthyl)ethyl, 1-(2-naphthyl)ethyl, 2-(1-naphthyl)ethyl, 2-(2-naphthyl)ethyl, or 9-fluorenylmethyl.

The "Het" group comprises groups containing 3, 4, 5, 6, 7, 8, 9, or 10 ring atoms in the parent monocyclic or bicyclic heterocyclic ring system. In monocyclic Het groups, the heterocyclic ring preferably is a 3-membered, 4-membered, 5-membered, 6-membered, or 7-membered ring, particularly preferably, a 5-membered or 6-membered ring. In bicyclic Het groups, preferably two fused rings are present, one of which is a 5-membered ring or 6-membered heterocyclic ring and the other of which is a 5-membered or 6-membered heterocyclic or carbocyclic ring, i.e., a bicyclic Het ring preferably contains 8, 9, or 10 ring atoms, more preferably 9 or 10 ring atoms.

Het comprises saturated heterocyclic ring systems which do not contain any double bonds within the rings, as well as mono-unsaturated and poly-unsaturated heterocyclic ring systems which contain one or more, for example, one, two, three, four, or five, double bonds within the rings provided that the resulting system is stable. Unsaturated rings may be non-aromatic or aromatic, i.e., double bonds within the rings in the Het group may be arranged in such a manner that a conjugated pi electron system results. Aromatic rings in a Het group may be 5-membered or 6-membered rings, i.e., aromatic groups in a Het group contain 5 to 10 ring atoms, and are in accordance by definition with Hückel's rule of aromaticity, that those systems defined as aromatic must have $4n+2\pi$ electrons (n=1, 2, etc.). Aromatic rings in a Het group thus comprise 5-membered and 6-membered monocyclic heterocycles and bicyclic heterocycles composed of two 5-membered rings, one 5-membered ring, and one 6-membered ring, or two 6-membered rings. In bicyclic aromatic groups in a Het group, one or both rings may contain heteroatoms. Aromatic Het groups may also be referred to by the customary term heteroaryl for which all the definitions and explanations above and below relating to Het correspondingly apply.

Unless stated otherwise, in the Het groups and any other heterocyclic groups, preferably 1, 2, 3, or 4 identical or different ring heteroatoms selected from nitrogen, oxygen, and sulfur are present. Particularly preferably, in these groups 1 or 2 identical or different ring heteroatoms selected from nitrogen, oxygen, and sulfur are present. The ring heteroatoms can be present in any desired number and in any position with respect to each other provided that the resulting heterocyclic system is known in the art and is stable and suitable as a subgroup in a drug substance. Examples of parent structures of heterocycles from which the Het group can be derived are aziridine, oxirane, thiirane, azetidine, pyrrole, furan, thiophene, dioxole, imidazole, pyrazole, oxazole, isoxazole, thiazole, isothiazole, 1,2,3-triazole, 1,2,4-triazole, tetrazole, pyridine, pyran, thiopyran, pyridazine, pyrimidine, pyrazine, 1,2-oxazine, 1,3-oxazine, 1,4-oxazine, 1,2-thiazine, 1,3-thiazine, 1,4-thiazine, 1,2,3-triazine, 1,2,4-triazine, 1,3,5-triazine, azepine, 1,2-diazepine, 1,3-diazepine, 1,4-diazepine, indole, isoindole, benzofuran, benzothiophene, 1,3-benzodioxole, indazole, benzimidazole, benzoxazole, benzothiazole, quinoline, isoquinoline, chromane, isochromane, cinnoline, quinazoline, quinoxaline, phthalazine, pyridoimidazoles, pyridopyridines, pyridopyrimidines, purine, or pteridine, as well as ring systems which result from the listed heterocycles by fusion (or condensation) of a carbocyclic ring, for example, benzo-fused, cyclopenta-fused, cyclohexa-fused, or cyclohepta-fused derivatives of these heterocycles.

The Het residue may be bonded via any ring carbon atom, and in the case of nitrogen heterocycles, via any suitable ring nitrogen atom. Thus, for example, a pyrrolyl residue can be 1-pyrrolyl, 2-pyrrolyl, or 3-pyrrolyl, a pyrrolidinyl residue can be 1-pyrrolidinyl (=pyrrolidino), 2-pyrrolidinyl, or 3-pyrrolidinyl, a pyridyl residue can be 2-pyridyl, 3-pyridyl, or 4-pyridyl, and a piperidinyl residue can be 1-piperidinyl (=piperidino), 2-piperidinyl, 3-piperidinyl, or 4-piperidinyl. Furyl can be 2-furyl or 3-furyl, thienyl can be 2-thienyl or 3-thienyl, imidazolyl can be 1-imidazolyl, 2-imidazolyl, 4-imidazolyl, or 5-imidazolyl, 1,3-oxazolyl can be 1,3-oxazol-2-yl, 1,3-oxazol-4-yl, or 1,3-oxazol-5-yl, 1,3-thiazolyl can be 1,3-thiazol-2-yl, 1,3-thiazol-4-yl, or 1,3-thiazol-5-yl, pyrimidinyl can be 2-pyrimidinyl, 4-pyrimidinyl (=6-pyrimidinyl), or 5-pyrimidinyl, and piperazinyl can be 1-piperazinyl (=4-piperazinyl=piperazino) or 2-piperazinyl. Indolyl can be 1-indolyl, 2-indolyl, 3-indolyl, 4-indolyl, 5-indolyl, 6-indolyl, or 7-indolyl. Similarly, benzimidazolyl, benzoxazolyl, and benzothiazolyl residues can be bonded via the 2-position and via any of the positions 4, 5, 6, and 7, benzimidazolyl also via the 1-position. Quinolyl can be 2-quinolyl, 3-quinolyl, 4-quinolyl, 5-quinolyl, 6-quinolyl, 7-quinolyl, or 8-quinolyl, and isoquinolyl can be 1-isoquinolyl, 3-isoquinolyl, 4-isoquinolyl, 5-isoquinolyl, 6-isoquinolyl, 7-isoquinolyl, or 8-isoquinolyl. In addition to being bonded via any of the positions indicated for quinolyl and isoquinolyl, 1,2,3,4-tetrahydroquinolyl and 1,2,3,4-tetrahydroisoquinolyl can also be bonded via the nitrogen atoms in the 1-position and 2-position, respectively.

Unless stated otherwise, and irrespective of any specific substituents bonded to Het groups or any other heterocyclic groups which are indicated in the definition of compounds of the present invention, the Het group can be unsubstituted or substituted on ring carbon atoms with one or more, for example, one, two, three, four, or five, identical or different substituents like $(C_1-C_8)$-alkyl, in particular $(C_1-C_4)$-alkyl, $(C_1-C_8)$-alkyloxy, in particular $(C_1-C_4)$-alkyloxy, $(C_1-C_4)$-alkylthio, halogen, nitro, amino, $((C_1-C_4)$-alkyl)carbonylamino like acetylamino, trifluoromethyl, trifluoromethoxy, hydroxy, oxo, hydroxy-$(C_1-C_4)$-alkyl such as, for example, hydroxymethyl, 1-hydroxyethyl, or 2-hydroxyethyl, methylenedioxy, ethylenedioxy, formyl, acetyl, cyano, methylsulfonyl, hydroxycarbonyl, aminocarbonyl, $(C_1-C_4)$-alkyloxycarbonyl, optionally substituted phenyl, optionally substituted phenoxy, benzyl optionally substituted in the phenyl group, or benzyloxy optionally substituted in the phenyl group. The substituents can be present in any desired position provided that a stable molecule results. Of course an oxo group cannot be present in a fully aromatic ring. Some degree of aromaticity exists for cross conjugated rings like para-quinone, but it is less in magnitude than the aromaticity assigned to benzene itself of approximately 36 Kcal/M. Each suitable ring nitrogen atom in a Het group can independently of each other be unsubstituted, i.e., carry a hydrogen atom, or can be substituted, i.e., carry a substituent like $(C_1-C_8)$-alkyl, for example, $(C_1-C_4)$-alkyl such as methyl or ethyl, optionally substituted phenyl, phenyl-$(C_1-C_4)$-alkyl, for example, benzyl, optionally substituted in the phenyl group, hydroxy-$(C_2-C_4)$-alkyl such as, for example, 2-hydroxyethyl, acetyl, or another acyl group, methylsulfonyl or another sulfonyl group, aminocarbonyl, or $(C_1-C_4)$-alkyloxycarbonyl. Nitrogen heterocycles can also be present as N-oxides or as quaternary salts. Ring sulfur atoms can be oxidized to the sulfoxide or to the sulfone. Thus, for example, a tetrahydrothienyl residue may be present as S,S-dioxotetrahydrothienyl residue or a thiomorpholinyl residue like 4-thiomorpholinyl may be present as 1-oxo-4-thiomorpholinyl or 1,1-dioxo-4-thiomorpholinyl. A substituted Het group that can be present in a specific position of compounds of formula I can independently of other Het groups be substituted by substituents selected from any desired subgroup of the substituents listed before and/or in the definition of that group.

The explanations relating to the Het residue correspondingly apply to divalent Het residues including divalent heteroaromatic residues which may be bonded via any two ring carbon atoms and in the case of nitrogen heterocycles via any carbon atom and any suitable ring nitrogen atom or via any two suitable nitrogen atoms. For example, a pyridinediyl residue can be 2,3-pyridinediyl, 2,4-pyridinediyl, 2,5-pyridinediyl, 2,6-pyridinediyl, 3,4-pyridinediyl, or 3,5-pyridinediyl, a piperidinediyl residue can be, among others, 1,2-piperidinediyl, 1,3-piperidinediyl, 1,4-piperidinediyl, 2,3-piperidinediyl, 2,4-piperidinediyl, or 3,5-piperidinediyl, and a piperazinediyl residue can be, among others, 1,3-piperazinediyl, 1,4-piperazinediyl, 2,3-piperazinediyl, or 2,5-piperazinediyl. The above statements also correspondingly apply to the Het subgroup in the Het-alkyl-groups. Examples of such Het-alkyl-groups which can also be unsubstituted or substituted in the Het subgroup as well as in the alkyl subgroup, are (2-pyridyl)methyl, (3-pyridyl)methyl, (4-pyridyl)methyl, 2-(2-pyridyl)ethyl, 2-(3-pyridyl)ethyl, or 2-(4-pyridyl)ethyl.

Alkoxy as used herein means an alkyl-O— group in which the alkyl group is as previously described. Exemplary alkoxy groups include methoxy, ethoxy, n-propoxy, t-propoxy, n-butoxy, t-butoxy and polyethers including —O—$(CH_2)_2OCH_3$.

An acyl group is defined as a group —C(O)R where R is an alkyl or aryl radical and includes acetyl, trifluoroacetyl, benzoyl and the like.

An example of an amino group is $NR_1R_2$.

Where terms are used in combination, the definition for each individual part of the combination applies unless defined otherwise. For instance, arylalkylthio refers to an aryl group, as defined above, alkyl group as defined above, and a thio group. An example is alkylamino, which is defined as a nitrogen atom substituted with an alkyl of 1 to 12 carbon atoms. Also, thioalkyl, or alkythio as used herein means an alkyl-S— group in which the alkyl group is as previously described. Thioalkyl groups include thiomethyl and the like. Examples of alkylthio groups of compounds of the present invention includes those groups having one or more thio ether linkages and from 1 to about 12 carbon atoms, further examples have from 1 to about 8 carbon atoms, and still further examples have 1 to about 6 carbon atoms. Alkylthio groups having 1, 2, 3 or 4 carbon atoms are further examples.

Some of the compounds of the invention may have stereogenic centers. The compounds may, therefore, exist in at least two and often more stereoisomeric forms. The present invention encompasses all stereoisomers of the compounds whether free from other stereoisomers or admixed with other stereoisomers in any proportion and thus includes, for instance, racemic mixture of enantiomers as well as the diastereomeric mixture of isomers. Thus, when using the term compound, it is understood that all stereoisomers are included.

The compounds of the present invention may be obtained or used as inorganic or organic salts using methods known to those skilled in the art. It is well known to one skilled in the art that an appropriate salt form is chosen based on physical and chemical stability, flowability, hydroscopicity and solubility. Pharmaceutically acceptable salts of the present invention with an acidic moiety may be optionally formed from organic and inorganic bases. For example with alkali metals or alkaline earth metals such as sodium, potassium, lithium, calcium, or magnesium or organic bases and N-tetraalkylammonium salts such as N-tetrabutylammonium salts. Similarly, when a compound of this invention contains a basic moiety, salts may be optionally formed from organic and inorganic acids.

For example salts may be formed from acetic, propionic, lactic, citric, tartaric, succinic, fumaric, maleic, malonic, mandelic, malic, phthalic, hydrochloric, hydrobromic, phosphoric, nitric, sulfuric, methanesulfonic, naphthalenesulfonic, benzenesulfonic, toluenesulfonic, camphorsulfonic, and similarly known acceptable acids. The compounds can also be used in the form of esters, carbamates and other conventional prodrug forms, which when administered in such form, convert to the active moiety in vivo. When using the term compound herein, it is understood that all salts are included.

The present invention accordingly provides a pharmaceutical composition which comprises a compound of this invention in combination or association with a pharmaceutically acceptable carrier. In particular, the present invention provides a pharmaceutical composition which comprises an effective amount of a compound of this invention and a pharmaceutically acceptable carrier.

The term "pharmaceutically acceptable salt" as used herein is intended to include the non-toxic acid addition salts with inorganic or organic acids, e.g. salts with acids such as hydrochloric, phosphoric, sulfuric, maleic, acetic, citric, succinic, benzoic, fumaric, mandelic, p-toluene-sulfonic, methane-sulfonic, ascorbic, lactic, gluconic, trifluoroacetic, hydroiodic, hydrobromic, and the like. Examples of pharmaceutically acceptable salts include, but are not limited to, mineral or organic acid salts of basic residues such as amines; alkali or organic salts of acidic residues such as carboxylic acids; and the like.

Pharmaceutically acceptable salts of the compounds of the invention can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, p. 1418, the disclosure of which is hereby incorporated by reference.

B. Methods of Using the Compounds of the Present Invention

The method of the present invention includes administering the effective compounds described herein to people or animals by any route appropriate to the condition to be treated, as determined by one of ordinary skill in the art. Additionally, physiologically acceptable acid addition salts of compounds described herein are also useful in the methods of treating of the present invention.

For pharmaceutical use, the compounds described herein may be taken up in pharmaceutically acceptable carriers, such as, for example, solutions, suspensions, tablets, capsules, ointments, elixirs and injectable compositions. Pharmaceutical preparations may contain from 0.1% to 99% by weight of active ingredient. Preparations which are in single dose form, "unit dosage form", preferably contain from 20% to 90% active ingredient, and preparations which are not in single dose form preferably contain from 5% to 20% active ingredient. As used herein, the term "active ingredient" refers to compounds described herein, salts thereof, and mixtures of compounds described herein with other pharmaceutically active compounds. Dosage unit forms such as, for example, tablets or capsules, typically contain from about 0.05 to about 1.0 g of active ingredient.

Suitable routes of administering the pharmaceutical preparations include, for example, oral, rectal, topical (including dermal, buccal and sublingual), vaginal, parenteral (including subcutaneous, intramuscular, intravenous, intradermal, intrathecal and epidural) and by naso-gastric tube. It will be understood by those skilled in the art that the preferred route of administration will depend upon the condition being treated and may vary with factors such as the condition of the recipient.

According to the methods of the present invention, the effective compounds described herein may be administered alone or in conjunction with other pharmaceutically active compounds. It will be understood by those skilled in the art that pharmaceutically active compounds to be used in combination with the compounds described herein will be selected in order to avoid adverse effects on the recipient or undesirable interactions between the compounds. As used herein, the term "active ingredient" is meant to include compounds described herein when used alone or in combination with one or more additional pharmaceutically active compounds. The amount of the compounds described herein required for use in the various treatments of the present invention depend, inter alia, on the route of administration, the age and weight of the animal (e.g. human) to be treated and the severity of the condition being treated.

It is preferred to administer the compounds of the present invention as pharmaceutical formulations. Useful formulations comprise one or more active ingredients and one or more pharmaceutically acceptable carriers. The term "pharmaceutically acceptable" means compatible with the other ingredients of the formulation and not toxic to the recipient. Useful pharmaceutical formulations include those suitable for oral, rectal, nasal, topical, vaginal or parenteral administration, as well as administration by naso-gastric tube. The formulations may conveniently be prepared in unit dosage form and may be prepared by any method known in the art of pharmacy. Such methods include the step of bringing the active ingredient into association with the carrier, which may constitute one or more accessory ingredients. In general, the formulations are prepared by uniformly bringing the active ingredients into association with liquid carriers or finely divided solid carriers or both, and then, if necessary, shaping the product.

Administration of the compositions of the present invention may be for either a prophylactic or therapeutic use. When provided prophylactically, a compound of the present invention is provided in advance of any symptoms such as exposure to conditions indicative of the methods of treatment of the present invention.

Additionally, a compound of the present invention may be administered during or after treatment to help prevent the reoccurrence the condition. The prophylactic administration of the composition is intended as a preventive therapy and serves to either prevent the condition or arrest or reverse the progression of the condition.

When provided therapeutically the composition is provided at or after the onset of the condition. The therapeutic administration of the composition of this invention serves to attenuate or alleviate the condition or facilitate regression of the condition afflicting the individual. The term individual is intended to include any animal, preferably a mammal, and most preferably a human. Veterinary uses are intended to be encompassed by this definition.

In one embodiment of this invention, individuals at high risk for a particular condition treatable by a method of the present invention, or at high risk of reoccurrence of a condition or who have known risk factors are prophylactically treated with the methods and compositions described herein. By way of example, such individuals may include those with a familial history for either early or late onset of cancer, and individuals who are being or have been treated for a cancer or cancer-related illness.

The daily dose of the compound may be administered in a single dose or in portions at various hours of the day. Initially, a higher dosage may be required and may be reduced over time when the optimal initial response is obtained. By way of example, treatment may be continuous for days, weeks, or years, or may be at intervals with intervening rest periods. The dosage may be modified in accordance with other treatments the individual may be receiving. One of skill in the art will appreciate that individualization of dosage may be required to achieve the maximum effect for a given individual. It is further understood by one skilled in the art that the dosage administered to a individual being treated may vary depending on the individuals age, severity or stage of the disease and response to the course of treatment. One skilled in the art will know the clinical parameters to evaluate to determine proper dosage for the individual being treated by the methods described herein.

Additional pharmaceutical methods may be employed to control the duration of action. Controlled release preparations may be achieved through the use of polymer to complex or absorb the proteins or their derivatives. The controlled delivery may be exercised by selecting appropriate macromolecules (for example polyester, polyamino acids, polyvinyl, pyrrolidone, ethylenevinylacetate, methylcellulose, carboxymethylcellulose, or protamine sulfate) and the concentration of macromolecules as well as the methods of incorporation in order to control release. Alternatively, instead of incorporating these agents into polymeric particles, it is possible to entrap these materials in microcapsules prepared, for example, by coacervation techniques or by interfacial polymerization.

When oral preparations are desired, the component may be combined with typical carriers/excipients, such as lactose, sucrose, starch, talc magnesium stearate, crystalline cellulose, methyl cellulose, carboxymethyl cellulose, glycerin, sodium alginate or gum arabic among others. The only limitation with resect to the carrier is that it does not deleteriously react with the active compound or is not deleterious to the recipient thereof.

The pharmaceutical preparations can be sterilized and if desired mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously react with the active compounds.

As stated above, the administration of the compositions or of each individual component of the present invention may be for either a prophylactic or therapeutic purpose. The methods and compositions used herein may be used alone in prophylactic or therapeutic uses or in conjunction with additional therapies known to those skilled in the art in the prevention or treatment of cancer. Alternatively the methods and compositions described herein may be used as adjunct therapy.

It will be appreciated that the actual preferred amounts of active compounds used in a given therapy will vary according to the specific compound being utilized, the particular compositions formulated, the mode of application, the particular site of administration, etc. Optimal administration rates for a given protocol of administration can be readily ascertained by those skilled in the art using conventional dosage determination tests.

Cancer, as used herein includes, but is not limited to, malignant tumors, adenocarcinomas, carcinomas, sarcomas, malignant neoplasms, and leukemias. In particular epithelial cell derived cancers are intended to be encompassed by this invention. Examples of epithelial cell derived cancers that may be treated by the methods described herein include, but are not limited to, breast cancer, colon cancer, ovarian cancer, lung cancer or prostate cancer. Such cancers may be caused by, chromosomal abnormalities, degenerative growth and developmental disorders, mitogenic agents, ultraviolet radiating (UV), viral infections, oncogenes, mutations in genes, in-appropriate expression of a gene and presentation on a cell, or carcinogenic agent.

EXPERIMENTAL DESCRIPTION/EXAMPLES/PREPARATION OF COMPOUNDS OF THE PRESENT INVENTION

This section is presented as the best mode and for exemplary purposes. Specifically, the information and examples provided herein are intended to demonstrate certain embodiments of the present invention and not to be construed as limiting the scope of the present invention.

Example 1

Preparation of Compounds of the Present Invention

This example demonstrates how compounds of the present invention may be made. Starting halogen-substituted resorcinol derivatives A1-4 (in the chart, below) may be synthesized by previously reported methods, while A5 and A6 and all phenylacetic acids B1-29 were commercially available. The synthetic sequence for the isoflavone library is depicted in Scheme 1. In the first step, Friedel-Crafts acylation of resorcinol derivatives A1-6 with substituted phenyl acetic acids B1-29 was carried out in the presence of $BF_3Et_2O$. The resulting intermediates I(A1-6,B1-29) were subjected to Vilsmeier-Haack cyclization to furnish the final products P(A1-6,B1-29). The reaction conditions were optimized first, and the library 6×29 of isoflavones was generated using a Quest 210 (Argonaut Technologies Inc., CA).

The following chart shows compounds that may be used as building blocks for embodiments of the present invention. In the chart, halogen-substituted resorcinol derivatives are indicated as A1-6, and phenylacetic acid derivatives are indicated as B1-29.

| Compd. | R |
|---|---|
| B1 | H |
| B2 | 3,4-di-OH |
| B3 | 3-Cl-4-OH |
| B4 | 3-F-4-OH |
| B5 | 3-OH |
| B6 | 3-$NO_2$ |
| B7 | 4-$NMe_2$ |
| B8 | 4-Cl |
| B9 | 4-F |

-continued

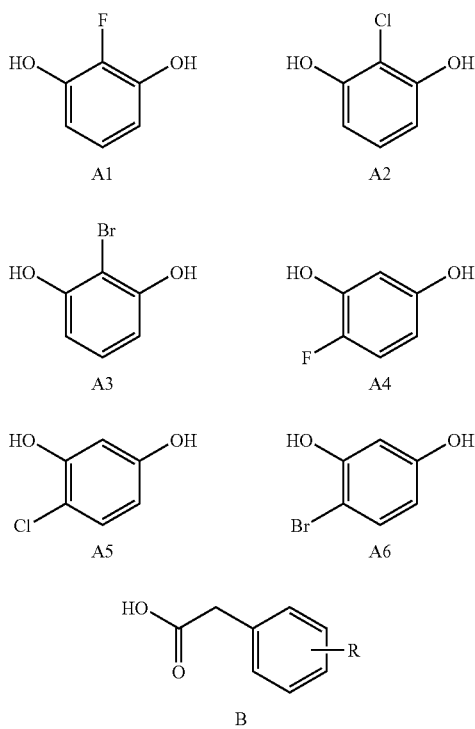

| Compd. | R |
|---|---|
| B10 | 4-OH |
| B11 | 4-OMe |
| B12 | 4-$NO_2$ |
| B13 | 3,4-di-OMe |
| B14 | 4-$CF_3$ |
| B15 | 4-$NH_2$ |
| B16 | 4-Ph |
| B17 | 4-Br |
| B18 | 4-OEt |
| B19 | 3-Me |
| B20 | 4-Me |
| B21 | 3,4-di-Cl |
| B22 | 3,4-di-F |
| B23 | 3,5-di-F |
| B24 | 3-$CF_3$ |
| B25 | 3-$NH_2$ |
| B26 | 3-Br |
| B27 | 3-Cl |
| B28 | 3-F |
| B29 | 3-OMe |

During the parallel synthesis of embodiments of the present invention, a slight excess of phenyl acetic acids was used in order to ensure complete consumption of the resorcinols. After on-line liquid-liquid extraction and solution drying/filtration, further purification was conducted employing a short plug of silica gel in parallel fashion under reduced pressure. All the products were analyzed by mass spectra and HPLC, and the results are summarized in the following Example, below. Overall yields based on tared weight ranged from 6 to 86%, and purities were greater than 70%.

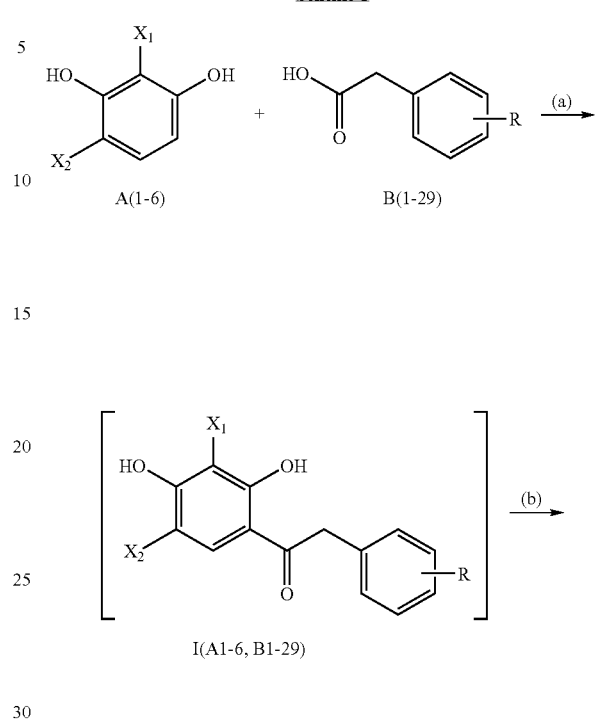

Scheme 1

Reagents: (a) $BF_3Et_2O$; (b) DMF, $MeSO_2Cl$.

While this method was found to be generally applicable with some modifications to time and temperature, the conflicting nature of having a basic moiety such as an amine attached to the nucleus of the ring system during ring cyclization under highly acidic conditions (e.g. synthesis of 9) became apparent. Such chemistry may not be generally suitable for parallel synthesis of amine substituted products or protonatable heterocyclic ring systems. Therefore, other methods have been developed for construction of chroman-4-ones having acid sensitive, or acid reactive groups as shown in Scheme 2 and 3.

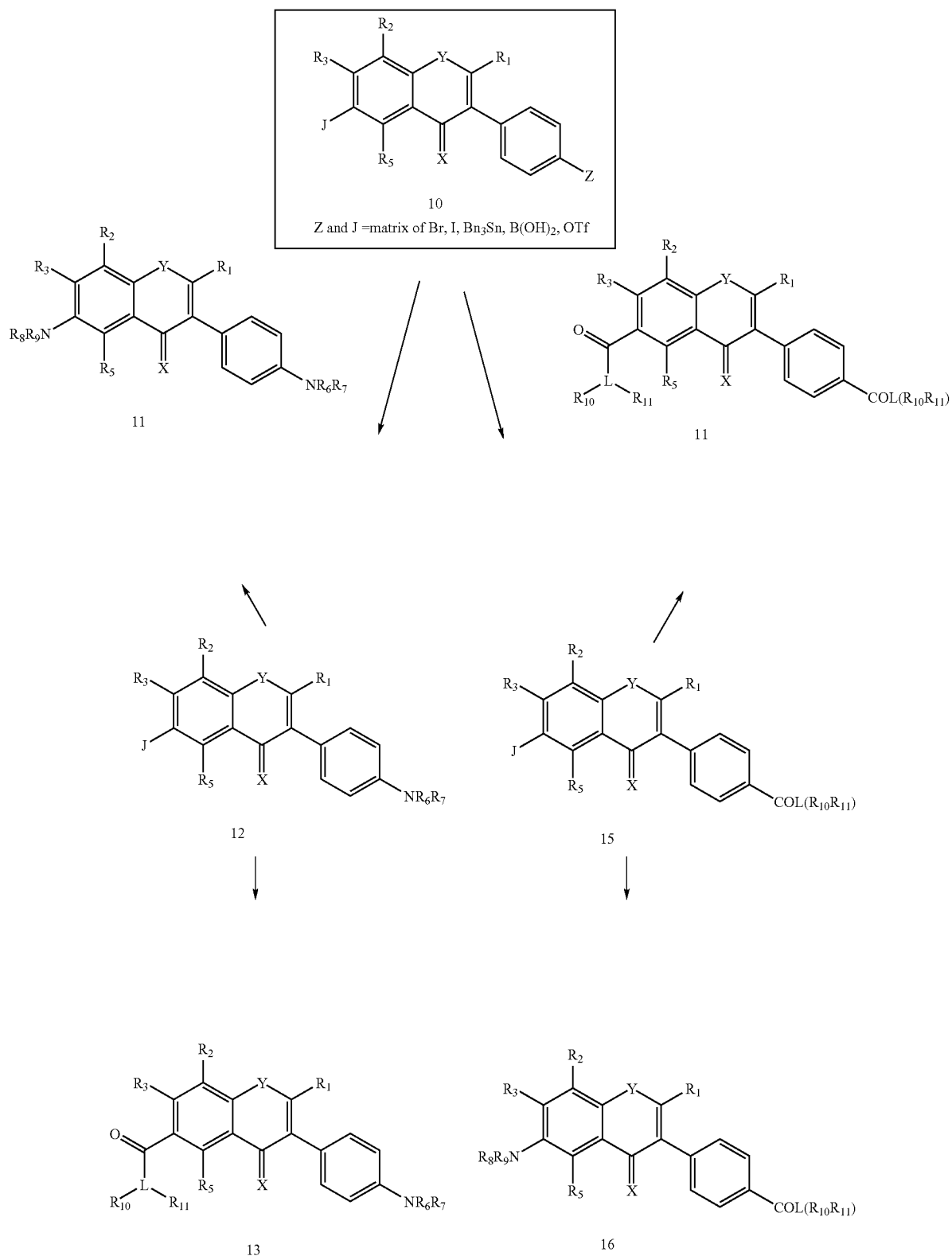

L is N or C; $R_{10}$ and $R_{11}$ are independent from one another and have the same definition as the above-defined R groups.

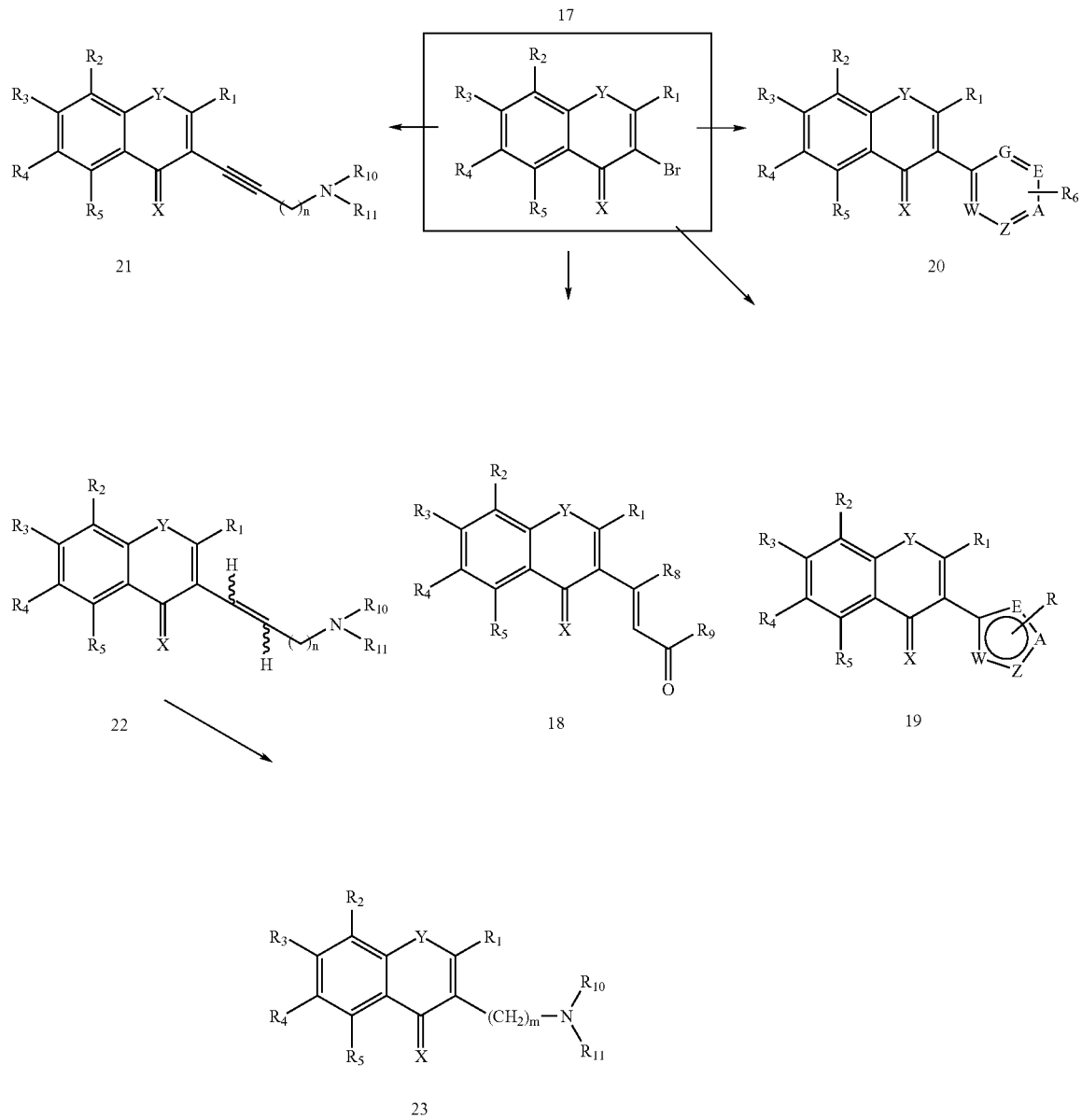

Scheme 3

For example, as shown in Scheme 2, a 4'-bromo substituted isoflavone could serve as a gateway compound for introduction of amines and other polar groups to a preformed chromanone ring system, avoiding the problematic ring construction step in the presence of a basic moiety. The amine addition step occurs readily for example by Pd(0) catalyzed coupling of 10 (or 17 in Scheme 3) either primary or secondary amines or as the boronate amides $B(NRR_1)_3$. It may be desirable to prepare libraries by attaching the 7-phenol to a resin such as a Wang resin, via the Wang bromide resin, and then conduct reaction and easily workup libraries before liberation from the solid matrix. The adduct amines, if removed by HCl, would be obtained as HCl salts. This is shown in Scheme 4. Additionally, Pd(II) complexes can be used with appropriate ligation and reductive conditions such that reaction occurs directly with free primary or secondary amines. This protocol allows one to generate secondary or tertiary amine analogs such as 27 without air sensitive reagents or the need for a separate boron reagent for every amine. Experimental details are provided in example 4.

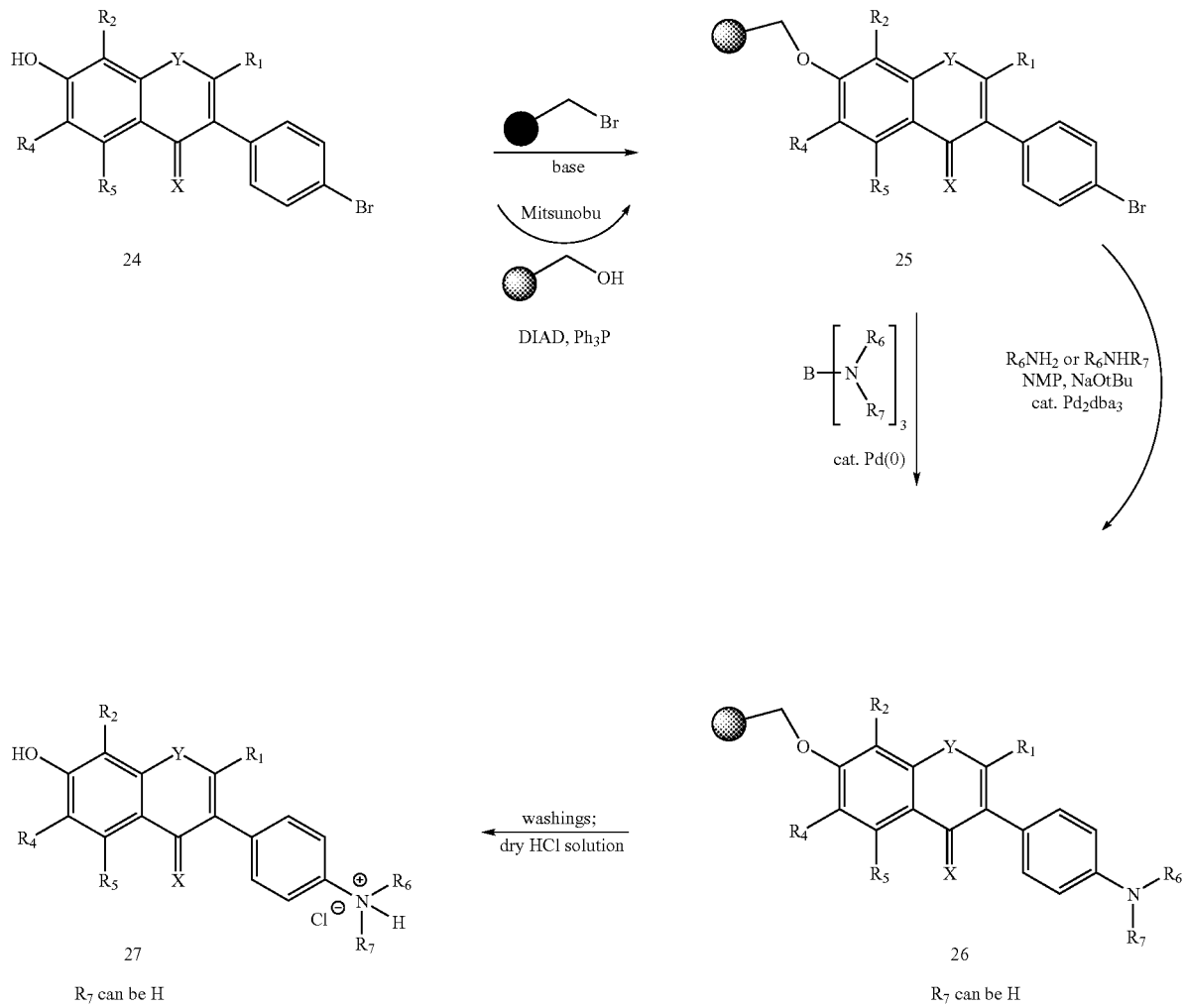

Scheme 4

An advantage of this approach is that the various R groups can be modified as required to achieve substantial diversity in the design of compounds of the present invention. For example, $R_1$ could be a protected hydroxyl group that could be converted to a triflate for further Pd(0) coupling chemistry at some point while still attached to the solid phase matrix. The bromoisoflavone 24 can be made by routine chemistry, as outlined in Scheme 1, as well as other methods.

Although acceptable embodiments of the present invention, the present inventor found that syntheses starting with bromoresorcinols led to poor reactivity and lower yields, compared to fluoro and chloro analogs. Without being bound by theory, this is presumably due to the increased sensitivity of C—Br bonds to the reaction conditions. The $IC_{50}$ values reported in Table 1 indicate that several of the halogenated isoflavones possess significant antigiardial activity. Overall, a fluoro substituent at C-8 of the isoflavone ring system displayed a substantial effect in antigiardial activity. However, compounds having a bromo substituent at C-8 did not show much bioactivity. Without being bound by theory, since the fluorine is considered to be as small as hydrogen in size and has higher electronegativity than the bromine, it is conceivable that electronic factors would be responsible for these results. Most of halogen substitutions at C-6 yielded less active or inactive (NA) analogs, which indicates, in general, that electron-withdrawing groups such as halogens at C-6 are not well-tolerated for antigiardial potency. As for the phenyl ring on C-3 of the isoflavone structure, compounds with a 4'-methoxy substrate showed enhanced potency in the antigiardial assay (P(A1,B11) and P(A3,B11)). Also, small hydrophobic substituents such as 3'-methyl (P(A1,B19), P(A3,B19), and P(A4,B19)) and 3'-fluoro (P(A3,B28) and P(A6,B28)) substrates were found to be preferable for enhanced potency. Regardless of the halogens on C-6 or C-8, incorporation of a hydrophobic bulky group on the phenyl ring at the C-4' position is not preferred due to less activity (P(A1,B16), P(A4,B16), P(A5,B16), and P(A6,B16)), implying the existence of a size-limited region in the binding pocket. The 4'-methoxy compounds, P(A1,B11) and P(A4,B11), had the lowest ClogP values (3.05 for both) and were therefore expected to provide an improvement in aqueous solubility. Of these two cases, only P(A1,B11) exhibited desirable bioactivity. The aqueous solubility and intrinsic oral bioavailability of P(A1,B11) are currently under examination.

Example 2

MS, HPLC, and Antigiardial Screening Results of Embodiments of the Present Invention

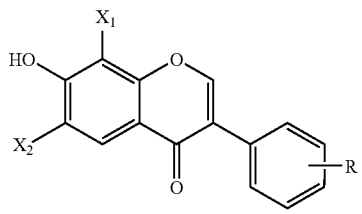

| Entry | Compd. | $X_1$ | $X_2$ | R | $[M + H]^+$ Calcd | $[M + H]^{+a}$ Found | Purity[b] (%) | $IC_{50}$ (μg/mL) |
|---|---|---|---|---|---|---|---|---|
| 1 | P(A1,B1) | F | H | H | 257 | 257 | 93 | <1.1 |
| 2 | P(A1,B8) | F | H | 4'-Cl | 291 | 291 | 92 | >10.0 |
| 3 | P(A1,B9) | F | H | 4'-F | 275 | 275 | 94 | >10.0 |
| 4 | P(A1,B11) | F | H | 4'-OMe | 287 | 287 | 87 | <1.1 |
| 5 | P(A1,B16) | F | H | 4'-Ph | 333 | 333 | >99 | NA |
| 6 | P(A1,B17) | F | H | 4'-Br | 335 | 335 | >99 | >10.0 |
| 7 | P(A1,B18) | F | H | 4'-OEt | 301 | 301 | >99 | 8.8 |
| 8 | P(A1,B19) | F | H | 3'-Me | 271 | 271 | >99 | <1.1 |
| 9 | P(A1,B20) | F | H | 4'-Me | 271 | 271 | >99 | <1.1 |
| 10 | P(A1,B22) | F | H | 3',4'-di-F | 293 | 293 | 81 | <1.1 |
| 11 | P(A1,B27) | F | H | 3'-Cl | 291 | 291 | >99 | <1.1 |
| 12 | P(A2,B1) | Cl | H | H | 273 | 273 | 95 | 1.7 |
| 13 | P(A2,B8) | Cl | H | 4'-Cl | 307 | 307 | 84 | 4.5 |
| 14 | P(A2,B9) | Cl | H | 4'-F | 291 | 291 | 92 | >10.0 |
| 15 | P(A2,B11) | Cl | H | 4'-OMe | 303 | 303 | 78 | >10.0 |
| 16 | P(A2,B17) | Cl | H | 4'-Br | 351 | 351 | 97 | 5.7 |
| 17 | P(A2,B18) | Cl | H | 4'-OEt | 317 | 317 | 81 | >10.0 |
| 18 | P(A2,B19) | Cl | H | 3'-Me | 287 | 287 | 75 | >10.0 |
| 19 | P(A2,B20) | Cl | H | 4'-Me | 287 | 287 | 72 | >10.0 |
| 20 | P(A2,B22) | Cl | H | 3',4'-di-F | 309 | 309 | 75 | 3.7 |
| 21 | P(A2,B23) | Cl | H | 3',5'-di-F | 309 | 309 | 94 | <1.1 |
| 22 | P(A2,B26) | Cl | H | 3'-Br | 351 | 351 | 97 | <1.1 |
| 23 | P(A2,B27) | Cl | H | 3'-Cl | 307 | 307 | 97 | 1.7 |
| 24 | P(A2,B28) | Cl | H | 3'-F | 291 | 291 | 98 | 5.2 |
| 25 | P(A2,B29) | Cl | H | 3'-OMe | 303 | 303 | 81 | 4.8 |
| 26 | P(A3,B1) | Br | H | H | 317 | 317 | 83 | 1.6 |
| 27 | P(A3,B8) | Br | H | 4'-Cl | 351 | 351 | 93 | 1.9 |
| 28 | P(A3,B9) | Br | H | 4'-F | 335 | 335 | 83 | 6.8 |
| 29[c] | P(A3,B10) | Br | H | 4'-OEt | 361 | 361 | 83 | 9.3 |
| 30 | P(A3,B11) | Br | H | 4'-OMe | 347 | 347 | 76 | <1.1 |
| 31 | P(A3,B17) | Br | H | 4'-Br | 395 | 395 | >99 | >10.0 |
| 32 | P(A3,B19) | Br | H | 3'-Me | 331 | 331 | >99 | <1.1 |
| 33 | P(A3,B20) | Br | H | 4'-Me | 331 | 331 | 90 | 3.9 |
| 34 | P(A3,B27) | Br | H | 3'-Cl | 351 | 351 | 85 | 1.9 |
| 35 | P(A3,B28) | Br | H | 3'-F | 335 | 335 | 93 | <1.1 |
| 36 | P(A4,B1) | H | F | H | 257 | 257 | >99 | 6.2 |
| 37[c] | P(A4,B5) | H | F | 3'-OEt | 301 | 301 | >99 | NA |
| 38 | P(A4,B8) | H | F | 4'-Cl | 291 | 291 | >99 | 6.4 |
| 39 | P(A4,B9) | H | F | 4'-F | 275 | 275 | 80 | >10.0 |
| 40[c] | P(A4,B10) | H | F | 4'-OEt | 301 | 301 | >99 | NA |
| 41 | P(A4,B11) | H | F | 4'-OMe | 287 | 287 | 73 | >10.0 |
| 42 | P(A4,B16) | H | F | 4'-Ph | 333 | 333 | >99 | NA |
| 43 | P(A4,B17) | H | F | 4'-Br | 335 | 335 | >99 | 9.0 |
| 44 | P(A4,B19) | H | F | 3'-Me | 271 | 271 | >99 | <1.1 |
| 45 | P(A4,B20) | H | F | 4'-Me | 271 | 271 | >99 | >10.0 |
| 46 | P(A4,B21) | H | F | 3',4'-di-Cl | 325 | 325 | 92 | >10.0 |
| 47 | P(A4,B22) | H | F | 3',4'-di-F | 293 | 293 | >99 | 9.4 |
| 48 | P(A4,B28) | H | F | 3'-F | 275 | 275 | >99 | 4.3 |
| 49 | P(A5,B1) | H | Cl | H | 273 | 273 | >99 | NA |
| 50 | P(A5,B9) | H | Cl | 4'-F | 291 | 291 | >99 | NA |
| 51 | P(A5,B11) | H | Cl | 4'-OMe | 303 | 303 | 89 | NA |
| 52 | P(A5,B16) | H | Cl | 4'-Ph | 349 | 349 | 79 | NA |
| 53 | P(A5,B17) | H | Cl | 4'-Br | 351 | 351 | >99 | >10.0 |
| 54 | P(A5,B18) | H | Cl | 4'-OEt | 317 | 317 | >99 | NA |
| 55 | P(A5,B19) | H | Cl | 3'-Me | 287 | 287 | >99 | 2.5 |
| 56 | P(A5,B20) | H | Cl | 4'-Me | 287 | 287 | >99 | NA |
| 57 | P(A5,B21) | H | Cl | 3',4'-di-Cl | 341 | 341 | >99 | 9.8 |
| 58 | P(A5,B22) | H | Cl | 3',4'-di-F | 309 | 309 | >99 | NA |

-continued

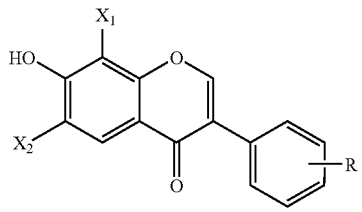

| Entry | Compd. | $X_1$ | $X_2$ | R | [M + H]$^+$ Calcd | [M + H]$^{+a}$ Found | Purity[b] (%) | IC$_{50}$ (μg/mL) |
|---|---|---|---|---|---|---|---|---|
| 59 | P(A5,B23) | H | Cl | 3',5'-di-F | 309 | 309 | 90 | 6.7 |
| 60 | P(A5,B26) | H | Cl | 3'-Br | 351 | 351 | >99 | NA |
| 61 | P(A5,B27) | H | Cl | 3'-Cl | 307 | 307 | >99 | >10.0 |
| 62 | P(A5,B28) | H | Cl | 3'-F | 291 | 291 | 85 | NA |
| 63 | P(A6,B1) | H | Br | H | 317 | 317 | >99 | 5.0 |
| 64 | P(A6,B8) | H | Br | 4'-Cl | 351 | 351 | 89 | NA |
| 65 | P(A6,B9) | H | Br | 4'-F | 335 | 335 | >99 | NA |
| 66 | P(A6,B16) | H | Br | 4'-Ph | 393 | 393 | 74 | NA |
| 67 | P(A6,B19) | H | Br | 3'-Me | 331 | 331 | >99 | NA |
| 68 | P(A6,B20) | H | Br | 4'-Me | 331 | 331 | 93 | >10.0 |
| 69 | P(A6,B28) | H | Br | 3'-F | 335 | 335 | 91 | <1.1 |
| 70[d] | 9 | H | H | 4'-NMe$_2$ | 282 | 282 | >99 | <1.1 |
| 71 | metronidazole | | | | | | | 1.5 |
| 72 | furazolidone | | | | | | | 8.6 |

[a]Observed parent ion peaks via LC-MS analysis.
[b]Performed using UV detection at 254 nm.
[c]R groups were converted to OEt in the presence of BF$_3$Et$_2$O.
[d]Synthesized manually from resorcinol and B7.

Synthesis of compound 9 was manually accomplished with resorcinol and B7 using similar reaction conditions. As expected, the dimethylamino moiety in 9 confers enhanced solubility, especially in aqueous acidic solution.

Example 3

Preparation and Screening Compounds of the Present Invention

Preparation. All solvents were purchased as reagent grade, dried appropriately, and stored over dry 4 Å molecular sieves. Solvent and reagent transfers were accomplished via dried syringe, and all reactions were performed under argon atmosphere unless otherwise indicated. Analytical thin-layer chromatography was performed on precoated silica gel GF 250 microns from Analtech and visualized with a 254 nm UV light. Parallel silica gel chromatography was accomplished under reduced pressure using Supeldlean LC-SI 20 mL tubes from Supelco. Unless otherwise stated, all NMR spectra were recorded in DMSO-d$_6$ on a Bruker Avance DPX 400, using TMS as an internal standard. The chemical shifts are reported in parts per million (ppm) relative to TMS, and J values in Hz. Mass spectra were recorded on a ThermoQuest Finnigan AQA quadrupole LC-MS system, and high-resolution mass spectra (HRMS) were measured with a Bruker BioApex FIMS system by direct injection using an electrospray interface (ESI). Analytical HPLC was performed on an automated Waters Alliance system using a Symmetry C$_{18}$ column, 3.9× 150 mm i. d., 5 μm, and a flow rate of 1 mL/min.; $\lambda_{max}$=254 nm; mobile phase A: 0.05% TFA in H$_2$O and mobile phase B: 0.05% TFA in CH$_3$CN; linear gradient 10-90% B in 15 min.

Solution-phase parallel synthesis was performed on an Argonaut Quest 210 using 10 mL teflon reaction vessels (RVs) with microfrit. Halogenated resorcinols A1-6 (1 equiv., 0.10 mmol) and phenyl acetic acid derivatives B1-29 (1.1 equiv., 0.11 mmol) were added manually to each RV, and the RVs were maintained under argon. BF$_3$.Et$_2$O (1 mL) was added manually to each RV via syringe, and the manifolds were sealed. The reaction mixtures were agitated for 3-10 h at 90-100° C. to facilitate the Friedel-Craft acylations. After cooling to room temperature, all reactions were analyzed by TLC for completion. Thereafter, a mixture of DMF (0.5 mL) and MeSO$_2$Cl (0.1 mL), which had been stirred separately for 30 min., was transferred to each RV via syringe under argon. The reaction mixtures were agitated for 4-5 h at 75° C. Aqueous NaOAc (12% w/v, 2 mL) and ethyl acetate (1 mL×3) were added to each RV, and on line liquid-liquid extraction was carried out by agitating the biphasic solutions for 5 min. Combined organic layers were washed with water (2 mL×2) and brine (2 mL/×2) and dried over anhydrous sodium sulfate within the RVs. The mixtures were collected into 20 mL glass vials. Organic solvent was evaporated under vacuum to furnish the crude products, which were further purified on a short plug of silica gel in parallel fashion under reduced pressure, using hexane/ethyl acetate (80:20 v/v). The yields reported are the overall yields.

Example 4

Specific Synthesis of Amine Substituted Isoflavones by Parallel Synthesis Methods 1. General Procedure for Loading of Starting Material on Wang Resin:

To a suspension of Wang resin (1 g, 1.11 mmole/g, 100-200 mesh) in THF (10 ml), the isoflavone 1 (1.74 g, 5.5 mmoles) and triphenylphosphine (1.44 g, 5.5 mmoles) were added and gently stirred at 0° C. for 30 minutes. DIAD (1.11 g, 5.5 mmoles) was added drpwise and the mixture was stirred for 24 hours gradually allowing it to attain room temperature. The resin was collected by filtration and washed successively with THF (6×5 ml), 1:1 THF/water (6×5 ml), THF (6×5 ml), DCM (6×5 ml), 1:1 DCM/MeOH (6×5 ml), MeOH (6×5 ml), DCM (6×5 ml) and finally with ether. The resin was dried and used in the next step.

A) Weight of Resin with Compound=1.245 gm

Therefore percentage of compound loaded=1.245/1.328=93.7%

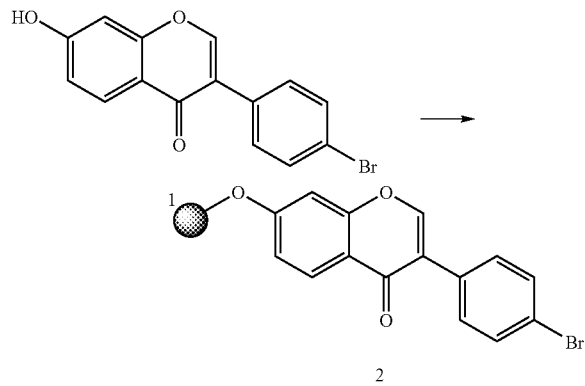

B) IR of the Resin also Confirmed that the Compound was Loaded on the Wang Resin 2. General Procedure for Reaction of Amines on Loaded Resin in Quest:

To a suspension of resin 2 (200 mg, 0.17 mmol) in anhydrous NMP (10 ml) in each reaction vessel, $Pd_2(dba)_3$ (7.7 mg, 0.0085 mmol, 5 mol %), ligand 3 (16.2 mg, 0.034 mmol, 20 mol %) and NaOt-Bu (122 mg, 1.275 mmol) were added and the reaction vessels were flushed with argon. Subsequently the amines (1.2 mmol) were added to the reaction vessel and the reaction mixture was heated to 100° C. for 30 hours. The resin was washed successively with DMF (6×5 ml), 1:1 DMF/water (6×5 ml), DMF (6×5 ml), DCM (6×5 ml), 1:1 DCM/MeOH (6×5 ml), MeOH (6×5 ml), DCM (6×5 ml) and ether (6×5 ml). The resin was dried and suspended in 1:3 TFA/DCM mixture and was stirred was 4 hours. The resin was filtered and washed with DCM (3×5 ml). The filterates were combined and $NaHCO_3$ was added and stirring till effervescence ceased. The filtrate was evaporated in vacuo.

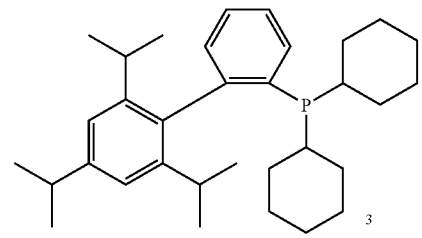

AMINES

| Reagent | Mol Wt. | Weight (g) | Volume (ml) | Density | eq | mmols | Product Code |
|---|---|---|---|---|---|---|---|
| p-anisidine | 123.16 | 0.125 | | | 6.000 | 1.02 | NMA-1 |
| N-methyl aniline | 107.16 | 0.109 | 0.110 | 0.989 | 6.000 | 1.02 | NMA-2 |
| phenethylamine | 121.18 | 0.123 | 0.130 | 0.962 | 6.000 | 1.02 | NMA-3 |
| allylamine | 57.1 | 0.058 | 0.076 | 0.763 | 6.000 | 1.02 | NMA-4 |
| dibutylamine | 129.25 | 0.131 | 0.172 | 0.761 | 6.000 | 1.02 | NMA-5 |
| morpholine | 87.12 | 0.088 | 0.090 | 0.996 | 6.000 | 1.02 | NMA-6 |
| pyrrolidine | 71.12 | 0.072 | 0.083 | 0.860 | 6.000 | 1.02 | NMA-7 |
| m-Cl-aniline | 127.57 | 0.130 | 0.110 | 1.206 | 6.000 | 1.02 | NMA-8 |
| benzylamine | 107.16 | 0.109 | 0.110 | 0.982 | 6.000 | 1.02 | NMA-9 |
| cyclohexylamine | 99.18 | 0.101 | 0.116 | 0.867 | 6.000 | 1.02 | NMA-10 |
| NaOt-Bu | 96.11 | 0.122 | | | 7.500 | 1.275 | |
| Pd2(dba)3 | 915.7 | 7.7 mg | | | 5 mol % | 0.0085 | |
| ligand | 476.72 | 16.2 mg | | | 20 mol % | 0.034 | |
| NMP | | | 3 ml | | | | |
| Br-isoflavone on resin | | 200 mg | | | | 0.17 | |

AMINES

| Reagent | Mol Wt | Weight (g) | Volume (ml) | Density | eq | mmol | Product Code |
|---|---|---|---|---|---|---|---|
| aniline | 93.13 | 0.095 | 0.093 | 1.021 | 6.000 | 1.02 | NMA-11 |
| butylamine | 73.14 | 0.075 | 0.100 | 0.737 | 6.000 | 1.02 | NMA-12 |
| isopropylamine | 59.11 | 0.060 | 0.087 | 0.694 | 6.000 | 1.02 | NMA-13 |
| diisopropylamine | 101.19 | 0.103 | 0.143 | 0.716 | 6.000 | 1.02 | NMA-14 |
| diethylamine | 73.14 | 0.075 | 0.110 | 0.704 | 6.000 | 1.02 | NMA-15 |
| piperidine | 85.15 | 0.086 | 0.099 | 0.861 | 6.000 | 1.02 | NMA-16 |
| 1-N-methylpiperazine | 100.17 | 0.102 | 0.112 | 0.903 | 6.000 | 1.02 | NMA-17 |
| piperonylamine | 151.17 | 0.154 | 0.127 | 1.214 | 6.000 | 1.02 | NMA-18 |
| 1-naphthalene methylamine | 157.22 | 0.160 | 0.150 | 1.073 | 6.000 | 1.02 | NMA-19 |

-continued

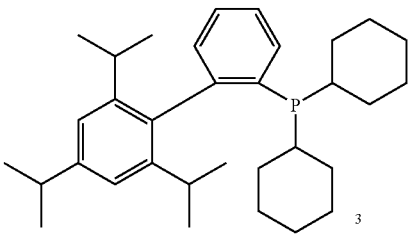

| | | | | | | | |
|---|---|---|---|---|---|---|---|
| O-anisidine | 123.15 | 0.125 | 0.115 | 1.092 | 6.000 | 1.02 | NMA-20 |
| sodium tert-butoxide | 96.11 | 0.122 | | | 7.500 | 1.275 | |
| Pd2(dba)3 | 915.7 | 7.7 mg | | | 5 mol % | 0.0085 | |
| ligand | 476.72 | 16.2 mg | | | 20 mol % | 0.034 | |
| NMP | | 3 ml | | | | | |
| Br-isoflavone on resin | | 200 mg | | | | 0.17 | |

Results:

| PRODUCT CODE | MOLECULAR WEIGHT | MOLECULAR FORMULA | WEIGHT (mg) | % YIELD | PURITY (%) |
|---|---|---|---|---|---|
| NMA-1 | 359 | $C_{22}H_{17}NO_4$ | 19 mg | 31.14 | 97.29 |
| NMA-2 | 343 | $C_{22}H_{17}NO_3$ | 11 mg | 19 | 99.10 |
| NMA-3 | 357 | $C_{23}H_{19}NO_3$ | 11 mg | 18.33 | 93.68 |
| NMA-4 | 293.11 | $C_{18}H_{15}NO_3$ | 9 mg | 18.07 | 92.60 |
| NMA-5 | 365.47 | $C_{23}H_{27}NO_3$ | 7 mg | 11.3 | 70.73* |
| NMA-6 | 323.12 | $C_{19}H_{17}NO_4$ | 20 mg | 36.36 | 93.66 |
| NMA-7 | 307.12 | $C_{19}H_{17}NO_3$ | 24 mg | 46.1 | 90.93 |
| NMA-8 | 363.07 | $C_{21}H_{14}ClNO_3$ | 18 mg | 30 | 74.26* |
| NMA-9 | 343.12 | $C_{22}H_{17}NO_3$ | 23 mg | 39.6 | 92.47 |
| NMA10 | 335.15 | $C_{21}H_{21}NO_3$ | 10 mg | 17.5 | 45.04* |
| NMA-11 | 329.35 | $C_{21}H_{15}NO_3$ | 15 mg | 26.7 | 49.91** |
| NMA-12 | 309.36 | $C_{19}H_{19}NO_3$ | 12 mg | 22.6 | 69.10** |
| NMA-13 | 295.12 | $C_{18}H_{17}NO_3$ | 16.5 mg | 33.0 | 84.89** |
| NMA-14 | 337.41 | $C_{21}H_{23}NO_3$ | 22 mg | 38.5 | 83.4** |
| NMA-15 | 309.36 | $C_{19}H_{19}NO_3$ | 19 mg | 36.2 | 99.60 |
| NMA-16 | 321.14 | $C_{20}H_{19}NO_3$ | 16 mg | 29.3 | 74.5** |
| NMA-17 | 336.15 | $C_{20}H_{20}N_2O_3$ | 9 mg | 15.7 | 82.69** |
| NMA-18 | 387.38 | $C_{23}H_{17}NO_5$ | 6 mg | 9.2 | 82.98** |
| NMA-19 | 393.43 | $C_{26}H_{19}NO_3$ | 14 mg | 21.21 | 59.42** |
| NMA-20 | 359.37 | $C_{22}H_{17}NO_4$ | 18 mg | 29.5 | 71.33** |

*Amines were purified by column chromatography.
**Values are prior to purification.

Biological Screening. *Giardia intestinalis* (ATCC #30888) was maintained anaerobically in acid-washed borosilicate glass tubes in Keister's modified TYI-S-33 medium at 37° C. Subculturing was done every 48-72 h under a sterile biosafety hood. Tubes were chilled in an ice bath for 10 min. in order to detach the organisms, and 1 mL of cell suspension was added to 14 mL of fresh medium. To carry out the screening, a suspension of *Giardia* cells was prepared at a concentration of 100,000 cells/mL. 100 µL of the suspension was then added to each well of a Corning 96-well flat-bottomed tissue culture-treated plate. Blank wells received medium only. An additional 125 µL of medium was added to each well, and the plates were incubated at 37° C. for 24 h in an anaerobic chamber filled with nitrogen. After 24 h, 25 µL of test samples with concentrations of 10, 3.3, and 1.1 µg/mL was added in duplicate to test wells. The plates were further incubated at 37° C. for 24 h. The plates were then processed using a tetrazolium dye (XTT) procedure. Absorbance readings were taken at 450 nm with background at 630 nm subtracted. Final concentration that inhibits giardial growth by 50% ($IC_{50}$) was estimated graphically from the dose-response plot.

Example 5

Examples of Embodiments of the Present Invention

This Example sets forth chemical characteristics of embodiments of the present invention.

8-Chloro-7-hydroxy-3-phenylchromen-4-one (P(A2, B1)): 70% yield; mp 242-244° C.; $^1$H NMR (400 MHz, DMSO-$d_6$) δ 8.50 (s, 1H), 7.93 (d, 1H, J=8.4 Hz), 7.57 (d, 2H, J=5.9 Hz), 7.42-7.33 (m, 3H), 7.13 (d, 1H, J=8.4 Hz); HRMS: [M+Na]$^+$ Calcd. for $C_{15}H_9ClO_3$ 295.0132, Found 295.0150.

8-Bromo-7-hydroxy-3-phenylchromen-4-one (P(A3, B1)): 45% yield; mp 256-258° C. (lit. 253° C.); $^1$H NMR (400 MHz, DMSO-$d_6$) δ 8.54 (s, 1H), 7.98 (d, 1H, J=8.8 Hz), 7.58 (d, 2H, J=7.1 Hz), 7.45-7.36 (m, 3H), 7.13 (d, 1H, J=8.8 Hz); HRMS: [M+Na]$^+$ Calcd. for $C_{15}H_9BrO_3$ 338.9627, Found 338.9661.

6-Chloro-7-hydroxy-3-phenylchromen-4-one (P(A5, B1)): 48% yield; mp 279-280° C.; $^1$HNMR (400 MHz, DMSO-$d_6$) δ 8.40 (s, 1H), 7.98 (s, 1H), 7.54 (d, 2H, J=7.1 Hz), 7.43-7.34 (m, 3H), 7.05 (s, 1H); HRMS: [M+Na]$^+$ Calcd. for $C_{15}H_9ClO_3$ 295.0132, Found 295.0129.

6-Bromo-7-hydroxy-3-phenylchromen-4-one (P(A6, B1)): 17% yield; mp 296-297° C., dec.; $^1$H NMR (400 MHz, DMSO-$d_6$) δ 8.42 (s, 1H), 8.17 (s, 1H), 7.56 (d, 2H, J=7.5 Hz), 7.45-7.36 (m, 3H), 7.06 (s, 1H); HRMS: [M+Na]$^+$ Calcd. for $C_{15}H_9BrO_3$ 338.9627, Found 338.9608.

7-Hydroxy-3-[4-(4-methoxy-phenylamino)-phenyl]-chromen-4-one (NMA-1): 31.14% yield. $^1$HNMR (400 MHz, DMSO-$d_6$) δ 7.97 (d, 1H, J=3.6 Hz), 7.36 (d, 2H, J=8.4 Hz), 6.86(d, 2H, J=8.4 Hz), 7.36 (d, 2H, J=8.8 Hz), 7.055 (d, 2H, J=8.8 Hz), 6.92 (d, 2H, J=8.0 Hz), 6.84(s, 1H), 3.575 (s, 3H).

7-Hydroxy-3-[4-(N-methylphenylamino)-phenyl]-chromen-4-one (NMA-2): 19% yield. $^1$HNMR (400 MHz, DMSO-$d_6$) δ 7.94 (d, 1H, J=8.8 Hz), 6.37 (dd, 1H, J=2, 8.8 Hz), 6.24 (d, 1H, J=2 Hz), 7.23 (t, 2H, J=8.4, 7.2 Hz), 7.18 (d, 2H, J=8.0 Hz), 6.94 (m, 4H), 6.89 (t, 1H, J=7.4 Hz), 3.276 (s, 3H).

7-Hydroxy-3-[4-{N-(2-phenyl)ethyl}amino)-phenyl]-chromen-4-one (NMA-3): 18.33% yield. $^1$HNMR ($^1$HNMR (400 MHz, DMSO-$d_6$) δ 7.897 (σ, 1H), 7.57 (d, 2H, J=8.2 Hz), 7.33 (d, 2H, J=8.4 Hz), 7.27 (d, 1H, J=5.6 Hz), 7.0 (d, 1H, J=6 Hz), 6.87 (m, 3H), 6.837 (s, 1H), 6.68(d, 2H, J=8.4 Hz), 3.284 (t, 2H, J=6.8, 7.2 Hz), 2.83 (t, 2H, J=7.2, 7.2 Hz).

7-Hydroxy-3-[4{N-allylamino)-phenyl]-chromen-4-one (NMA-4): 18.07% yield. $^1$HNMR (400 MHz, DMSO-$d_6$) δ 8.206 (s, 1H), 7.92 (d, 1H, J=8 Hz), 7.04 (d, 1H, J=8 Hz), 7.23

(d, 2H, J=8 Hz), 6.89 (s, 1H), 6.50 (d, 2H, J=8 Hz), 4.012 (m, 3H), 3.81 (t, 2H, J=6.8, 7.0 Hz).

7-Hydroxy-3-[4-(N,N-dibutylamino)-phenyl]-chromen-4-one (NMA-5): 11.3% yield. $^1$HNMR (400 MHz, DMSO-d$_6$) δ 7.99 (d, 1H, J=7.8 Hz), 7.928 (s, 1H), 6.862 (s, 1H), 7.49 (d, 2H, J=8.4 Hz), 7.22 (d, 1H, J=8.0 Hz), 7.06 (d, 2H, J=8.4 Hz), 3.025(t, 2H, J=9.2, 9.6 Hz), 2.946 (t, 2H, J=8.6 Hz), 1.31 (m, 4H), 1.263 (t, 2H, J=6.8, 6.8 Hz), 1.15 (t, 2H, J=7.2, 7.2 Hz), 0.85 (m, 6H).

7-Hydroxy-3-[4-morpholino)-phenyl]-chromen-4-one (NMA-6): 36.36% yield. $^1$HNMR (400 MHz, DMSO-d$_6$) δ 8.159 (s, 1H), 7.81 (d, 1H, J=8.8 Hz), 7.10 (d, 2H, J=8.4 Hz), 6.81 (d, 2H, J=8 Hz), 6.309 (d, 1H, J=7.2 Hz), 6.183 (s, 1H), 3.696 (m, 4H), 3.023 (m, 4H).

7-Hydroxy-3-[4-pyrrolidino)-phenyl]-chromen-4-one (NMA-7): 46.1% yield. $^1$HNMR (400 MHz, DMSO-d$_6$) δ 7.83 (d, 1H, J=8.8 Hz), 7.625 (d, 1H, J=8.8 Hz), 7.5 (s, 1H), 7.34 (d, 2H, J=8.2 Hz), 6.853 (s, 1H), 6.39 (d, 2H, J=8 Hz), 3.14 (t, 2H, J=8.0, 8.4 Hz), 2.971 (t, 2H, J=8.2, 8.2 Hz), 1.886 (m, 4H)

7-Hydroxy-3-[4-(N-{3-chlorophenyl}amino)-phenyl]-chromen-4-one (NMA-8): 30% yield. $^1$HNMR (400 MHz, DMSO-d$_6$) δ 8.25(s, 1H), 7.98 (d, 1H, J=8.8 Hz), 7.48 (d, 2H, J=8 Hz), 7.38 (s, 1H), 7.226 (t, 1H, J=7.6, 8.0 Hz), 7.12 (d, 1H, J=8.4 Hz), 6.92 (d, 1H, J=8.4 Hz), 6.86 (s, 1H), 6.81 (d, 1H, J=7.6 Hz), 6.66 (d, 2H, J=8 Hz).

7-Hydroxy-3-[4-(N-benzylamino)-phenyl]-chromen-4-one (NMA-9): 39.6% yield. $^1$HNMR (400 MHz, DMSO-d$_6$) δ 7.85 (d, 2H, J=8.8 Hz), 7.65 (s, 1H), 7.25 (s, 1H), 7.16 (d, 2H, J=7.2 Hz), 7.13 (t, 2H, J=7.6, 8.0 Hz), 7.04 (t, 1H, J=6.4, 6.8 Hz), 6.82 (s, 1H), 6.69 (dd, 1H, J=2, 8.8 Hz), 6.45 (d, 2H, J=8 Hz), 4.14(s, 2H).

7-Hydroxy-3-[4-(N-cyclohexylamino)-phenyl]-chromen-4-one (NMA-10): 17.5% yield. $^1$HNMR (400 MHz, DMSO-d$_6$) δ 8.205 (s, 1H), 1.45 (d, 1H, J=8 Hz), 7.26 (d, 1H, J=8 Hz), 6.853 (s, 1H), 6.59 (d, 2H, J=8 Hz), 6.49 (d, 2H, J=8 Hz), 3.216 (m, 1H), 1.564 (m, 4H), 1.328 (m, 2H), 1.21(m, 4H).

7-Hydroxy-3-[4-phenylamino)-phenyl]-chromen-4-one (NMA-11): 26.7% yield. $^1$HNMR (400 MHz, DMSO-$_6$) δ 7.97 (d, 1H, J=8.4 Hz), 7.82 (d, 1H), 7.35 (d, 2H, J=8.4 Hz), 7.33 (m, 3H), 7.15 (d, 1H, J=8.4 Hz), 7.05 (d, 2H, J=8 Hz), 6.82 (s, 1H), 6.75 (d, 2H, J=8 Hz).

7-Hydroxy-3-[4-(N-butylamino)-phenyl]-chromen-4-one (NMA__12): 22.6% yield. $^1$HNMR (400 MHz, DMSO-d$_6$) δ 8.213 (s, 1H), 7.92 (d, 1H, J=8.4 Hz), 7.47 (d, 2H, J=8 Hz), 7.01 (d, 1H, J=8.4 Hz), 6.85 (s, 1H), 6.56 (d, 2H, J=8.4 Hz), 2.99 (t, 2H, J=7.6, 8 Hz), 1.5 (m, 4H), 1.15 (m, 3H).

7-Hydroxy-3-[4-(N-isopropylamino)-phenyl]-chromen-4-one (NMA-13): 33% yield $^1$HNMR (400 MHz, DMSO-d$_6$) δ 8.21 (s, 1H), 7.88 (d, 1H, J=7.6 Hz), 7.51 (d, 2H, J=7.6 Hz), 7.13 (d, 1H, J=8 Hz), 6.85 (s, 1H), 6.51 (d, 2H, J=8 Hz), 4.02 (m, 1H), 1.27 (d, 6H, J=8 Hz).

7-Hydroxy-3-[4-(N,N-diisopropylamino)-phenyl]-chromen-4-one (NMA-14): 38.5% yield. $^1$HNMR (400 MHz, DMSO-d$_6$) δ 8.29 (s, 1H), 7.91 (s, 1H), 7.60 (d, 1H, J=8 Hz), 7.21 (d, 1H, J=8 Hz), 7.31 (d, 2H, J=8.4 Hz), 6.54 (d, 2H, J=8.4 Hz), 3.986 (m, 2H), 1.21 (d, 12H, J=8.2 Hz).

7-Hydroxy-3-[4-(N,N-diethylamino)-phenyl]-chromen-4-one (NMA-15): 36.2% yield. $^1$HNMR (400 MHz, DMSO-d$_6$) δ 8.16 (s, 1H), 7.93 (d, 1H, J=8.4 Hz), 7.91 (d, 2H, J=8.4 Hz), 7.42 (d, 2H, J=8 Hz), 6.75 (s, 1H), 6.5 (d, 2H, J=8.4 Hz), 3.246 (q, 4H, J=6.8, 7.2, 6.8 Hz), 1.05 (t, 6H, J=6.8, 6.8 Hz).

7-Hydroxy-3-[4-piperidino)-phenyl]-chromen-4-one (NMA-16): 29.3% yield. $^1$HNMR (400 MHz, DMSO-d$_6$) δ 8.12 (s, 1H), 7.92 (d, 1H, J=8 Hz), 7.09 (d, 1H, J=8.4 Hz), 7.32 (d, 2H, J=8.4 Hz), 6.62 (d, 2H, J=8 Hz), 6.85 (s, 1H), 3.14 (t, 2H, J=8, 8.4 Hz), 3.05 (t, 2H, J=7.6, 8 Hz), 1.567 (m, 6H).

7-Hydroxy-3-[4-(N-methylpiperazino)phenyl]-chromen-4-one (NMA-17): 15.7% yield. $^1$HNMR (400 MHz, DMSO-d$_6$) δ 8.13 (s, 1H), 7.92 (d, 1H, J=8 Hz), 7.33 (d, 2H, J=7.6 Hz), 7.17 (d, 1H, J=8.4 Hz), 6.85 (s, 1H), 6.74 (d, 2H, J=8 Hz), 3.78 (m, 4H), 2.71 (s, 3H), 2.205 (m, 4H).

7-Hydroxy-3-[4-{N-(c-Benzo[1,3]dioxol-5-yl-methyl}amino)-phenyl]-chromen-4-one (NMA-18): 9.2% yield. $^1$HNMR (400 MHz, DMSO-d$_6$) δ 8.19 (s, 1H), 7.93 (d, 1H, J=7.6 Hz), 7.46 (d, 2H, J=8.4 Hz), 7.22 (d, 1H, J=7.6 Hz), 7.16 (d, 1H, J=8 Hz), 7.02 (s, 1H), 6.91 (s, 1H), 6.77 (d, 1H, J=8.4 Hz), 6.58 (d, 2H, J=8.4 Hz), 5.98 (s, 2H), 4.17 (s, 2H).

7-Hydroxy-3-[4-{(N-naphthalen-1-ylmethyl)amino}-phenyl]-chromen-4-one (NMA-19): 21.21% yield. $^1$HNMR (400 MHz, DMSO-d$_6$) δ 8.12 (s, 1H), 7.933 (d, 1H, J=8 Hz), 7.72 (m, 2H), 7.62 (d, 1H, J=7.6 Hz), 7.53 (d, 1H, J=8 Hz), 7.42 (d, 2H, J=8.4 Hz), 7.23 (m, 3H), 7.13 (d, 1H, J=7.6 Hz), 6.82 (s, 1H), 6.61 (d, 2H, J=8.4 Hz), 4.5 (s, 2H).

7-Hydroxy-3-[4-{(2-methoxyphenyl)amino}-phenyl]-chromen-4-one (NMA-20): 29.5% yield. $^1$HNMR (400 MHz, DMSO-d$_6$) δ 8.13 (s, 1H), 7.94 (d, 1H, J=7.6 Hz), 7.23 (d, 1H, J=8 Hz), 6.84 (s, 1H), 7.51 (d, 2H, J=8.4 Hz), 7.04 (d, 2H, J=8.4 Hz), 6.87 (m, 3H), 6.65 (d, 1H, J=8.4 Hz), 3.81 (s, 3H).

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the Specification and Example be considered as exemplary only, and not intended to limit the scope and spirit of the invention.

Unless otherwise indicated, all numbers expressing quantities of ingredients, properties such as reaction conditions, and so forth used in the Specification and claims are to be understood as being modified in all instances by the term "about." Accordingly, unless indicated to the contrary, the numerical parameters set forth in the Specification and Claims are approximations that may vary depending upon the desired properties sought to be determined by the present invention.

Notwithstanding that the numerical ranges and parameters setting forth the broad scope of the invention are approximations, the numerical values set forth in the experimental or example sections are reported as precisely as possible. Any numerical value, however, inherently contain certain errors necessarily resulting from the standard deviation found in their respective testing measurements.

Throughout this application, various publications, including journal articles and patents are referenced. All such references are incorporated herein by reference in their entirety.

We claim:

1. A compound of the following formula:

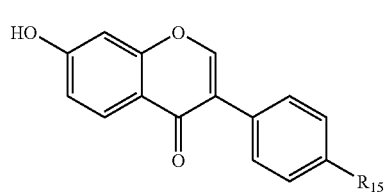

VII $R_{15}$ is N-substituted amino, of the following formula:
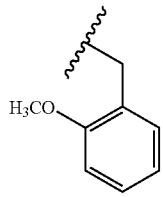
or,
HET; wherein HET is chosen from pyrrolidine, morpholine, piperazine, piperidine;
and pharmaceutically acceptable salts thereof.
2. A compound of claim 1, wherein HET is pyrrolidine, morpholine.
3. A compound of claim 1 having the following structure:
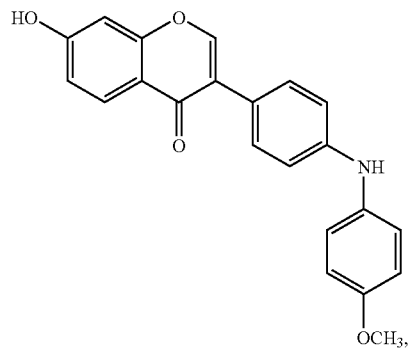
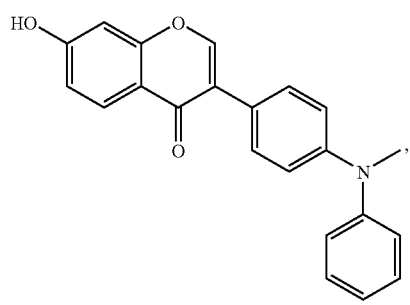
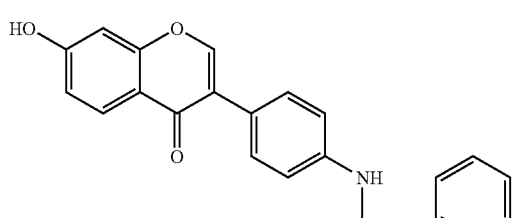
-continued
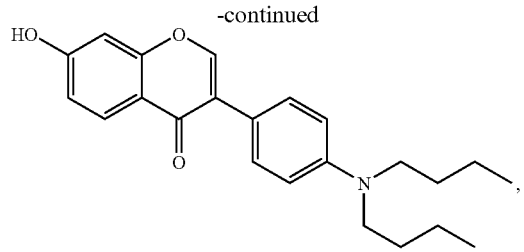
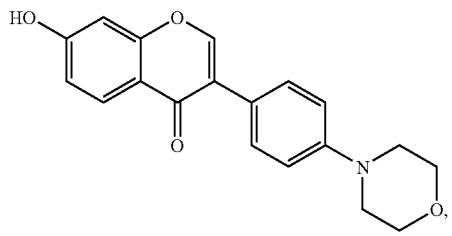
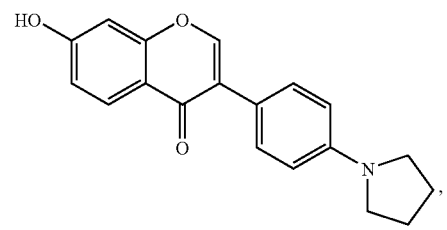
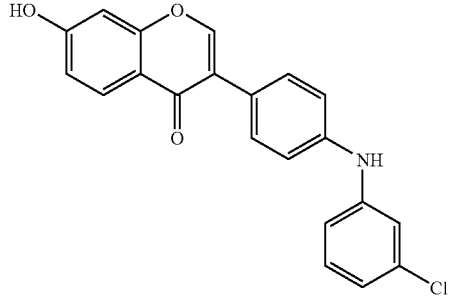
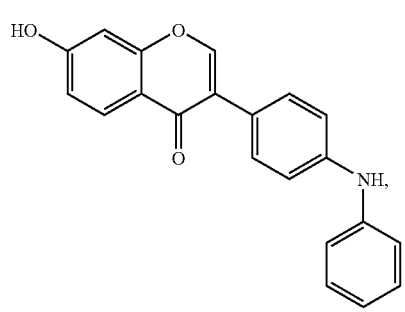

-continued
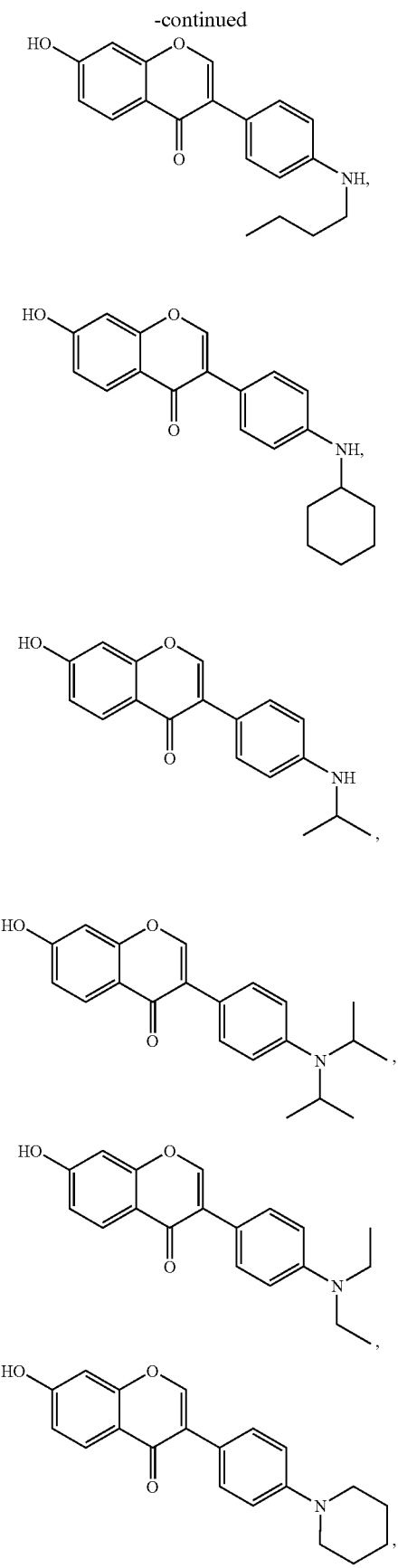
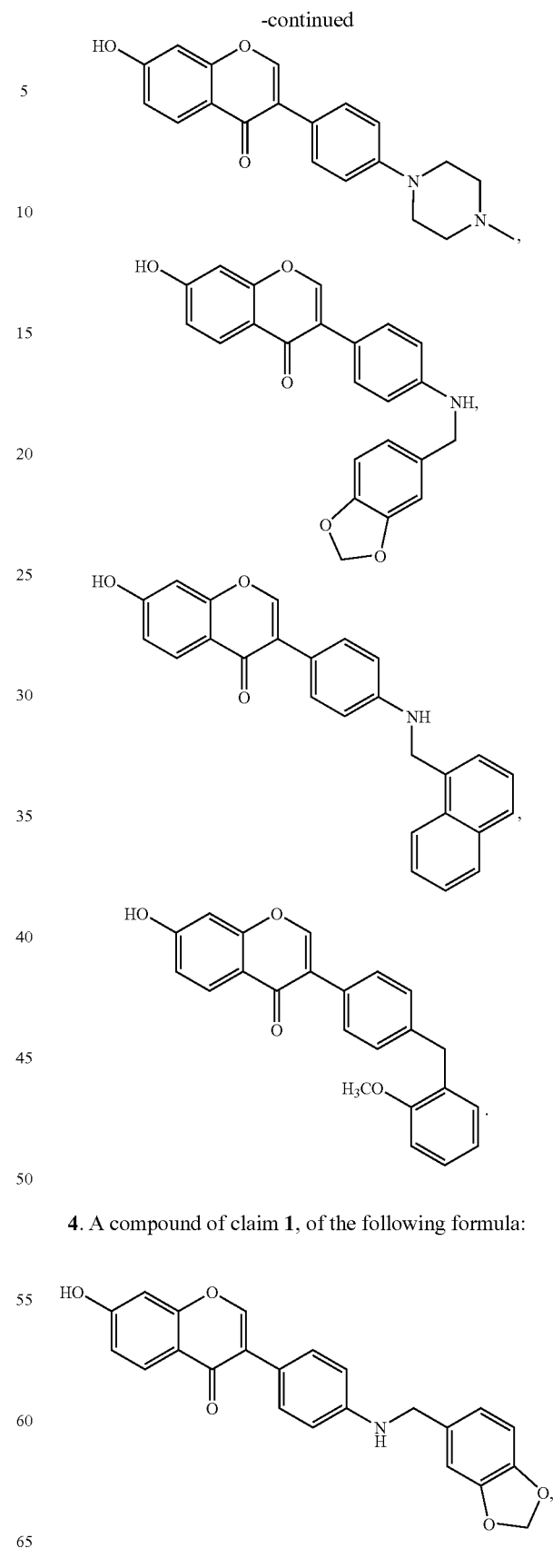
4. A compound of claim 1, of the following formula:
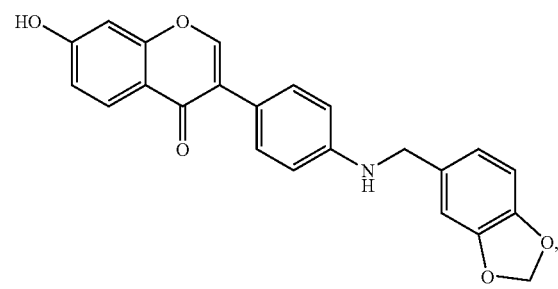
and pharmaceutically acceptable salts thereof.

5. A compound of claim 1, of the following formula:
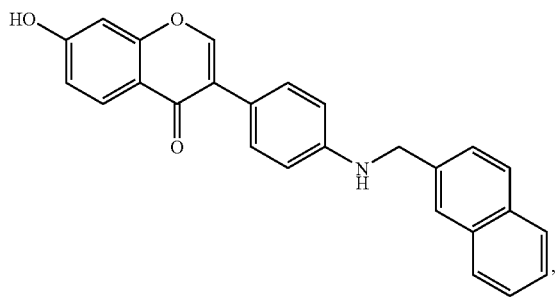
and pharmaceutically acceptable salts thereof.
6. A compound of claim 1, of the following formula:
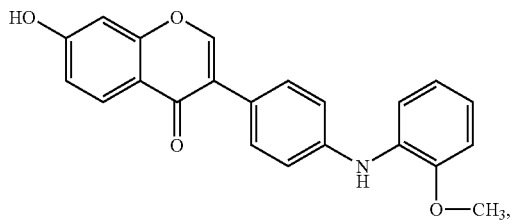
and pharmaceutically acceptable salts thereof.
* * * * *